US011426447B2

(12) United States Patent
Schulz et al.

(10) Patent No.: US 11,426,447 B2
(45) Date of Patent: Aug. 30, 2022

(54) NEUREGULIN FOR THE TREATMENT OF TUMORS OF THE NERVOUS SYSTEM

(71) Applicant: LEIBNIZ-INSTITUT FUR ALTERNSFORSCHUNG—FRITZ-LIPMANN-INSTITUT E.V. (FLI), Jena (DE)

(72) Inventors: Alexander Schulz, Jena (DE); Helen Morrison, Jena (DE)

(73) Assignee: LEIBNIZ-INSTITUT FUR ALTERNSFORSCHUNG—FRITZ-LIPMANN-INSTITUT E.V. (FLI), Jena (DE)

( * ) Notice: Subject to any disclaimer, the term of this patent is extended or adjusted under 35 U.S.C. 154(b) by 712 days.

(21) Appl. No.: 15/999,851

(22) PCT Filed: Apr. 19, 2017

(86) PCT No.: PCT/EP2017/059245
§ 371 (c)(1),
(2) Date: Aug. 20, 2018

(87) PCT Pub. No.: WO2017/182500
PCT Pub. Date: Oct. 26, 2017

(65) Prior Publication Data

US 2021/0213100 A1 Jul. 15, 2021

(30) Foreign Application Priority Data

Apr. 19, 2016 (EP) .................................... 16165991

(51) Int. Cl.
*A61K 38/18* (2006.01)
*A61P 35/00* (2006.01)

(52) U.S. Cl.
CPC .............. *A61K 38/18* (2013.01); *A61P 35/00* (2018.01)

(58) Field of Classification Search
None
See application file for complete search history.

(56) References Cited

U.S. PATENT DOCUMENTS 6,136,558 A * 10/2000 Ballinger ......... C07K 14/57509 435/252.3
9,168,297 B2 * 10/2015 Hearing .................. A61P 17/16
2011/0269682 A1 * 11/2011 Caggiano ................ A61P 25/28 514/9.6
2014/0088009 A1 * 3/2014 Ford ....................... A61P 25/00 514/8.3

FOREIGN PATENT DOCUMENTS

WO WO99/18976 * 4/1999 ............. A61K 38/18
WO 0189568 A1 11/2001
WO WO2007113366 * 10/2007 ......... A61K 38/1883
WO WO2011147981 * 12/2011 ............. A61K 38/18
WO 2012053076 A1 4/2012

OTHER PUBLICATIONS

Search for Neuregulin in the NCBI database. Accessed Apr. 21, 2021 (Year: 2021).*

Wen et al. Structural and functional aspects of the multiplicity of Neu differentiation factors. Mol. Cel. Biol. 1909-1919, 1994. (Year: 1994).*

Stonecypher et al., Activation of the neuregulin-1/ErbB signaling pathway promotes the proliferation of neoplastic Schwann cells in human malignant peripheral nerve sheath tumors. Oncogene, 24, 5589-5605, 2005. (Year: 2005).*

Gambarotta et al. , Neuregulin 1 isoforms could be an effective therapeutic candidate to promote peripheral nerve regeneration. Neural Regen. Res., 9, 1183-1185, 2014. (Year: 2014).*

Schulz et al., Neuronal merlin influences ERBB2 receptor expression on Schwann cells through neuregulin 1 type III signaling. Brain, 137, 420-432, 2014. (Year: 2014).*

Carroll et al., How Does the Schwann Cell Lineage Form Tumors in NF1? Glia 56, 1590-1605, 2008. (Year: 2008).*

Stove, C. et al., "Roles for neuregulins in human cancer", Clinical & Experimental Metastasis, 2004, pp. 665-684, vol. 21, © 2005 Springer; DOI: 10.1007/s10585-004-6917-6.

International Search Report dated Jul. 7, 2017 for International Application No. PCT/EP2017/059245 filed Apr. 19, 2017.

* cited by examiner

*Primary Examiner* — Elly-Gerald Stoica
(74) *Attorney, Agent, or Firm* — Blue Filament Law PLLC

(57) ABSTRACT

The invention relates to a polypeptide, wherein said polypeptide comprises or consists of an EGF-like domain of a neuregulin protein. The invention more over relates to a nucleic acid encoding for said polypeptide, a gene therapy vector comprising said nucleic acid and genetically modified cells expressing said polypeptide. The invention relates to the medical use of said polypeptide, said nucleic acid, said gene therapy vector or said cell for the treatment of tumours of the nervous system, in particular for the treatment of tumours of the cranial or peripheral nerves, tumours associated with neurofibromatosis, schwannomas, neurofibromas and malignant nerve sheath tumours.

15 Claims, 9 Drawing Sheets

Figure 1:
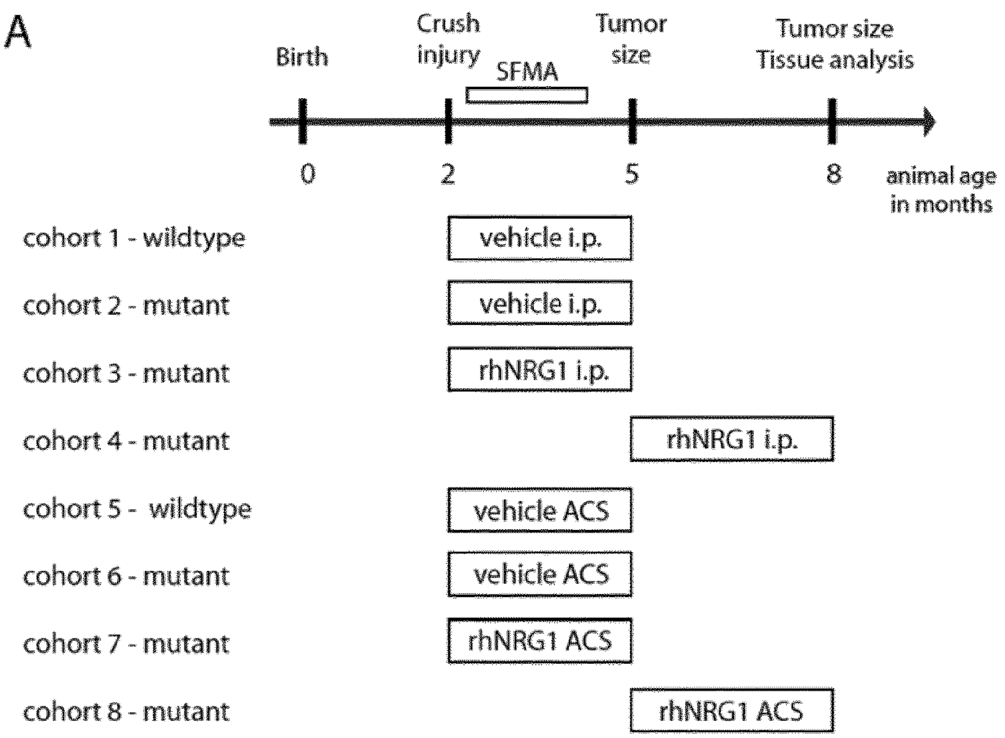
Figure 1:
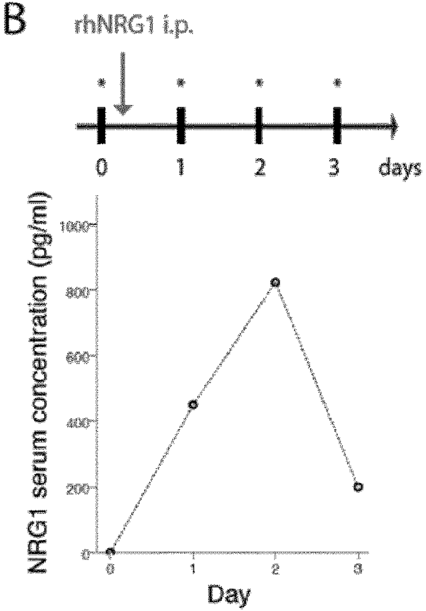
Figure 1:
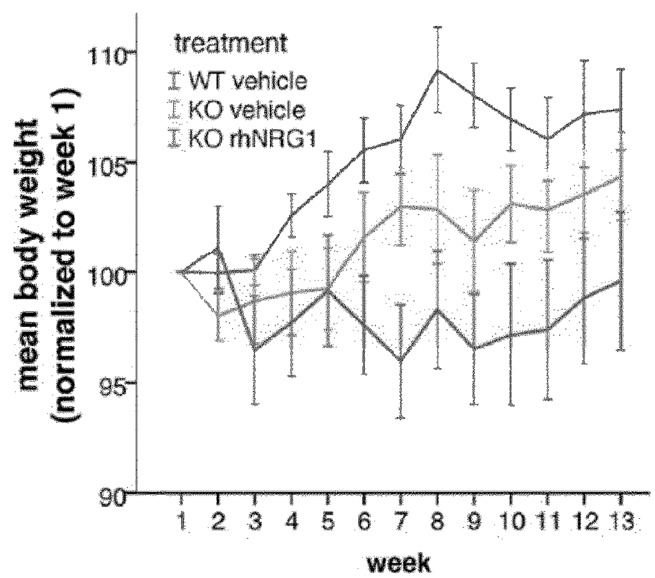

Specification includes a Sequence Listing.

NEUREGULIN FOR THE TREATMENT OF TUMORS OF THE NERVOUS SYSTEM

The invention relates to a polypeptide, wherein said polypeptide comprises or consists of an EGF-like domain of a neuregulin protein. The invention relates to a nucleic acid encoding for said polypeptide, a gene therapy vector comprising said nucleic acid and genetically modified cells expressing said polypeptide. The invention relates to the medical use of said polypeptide, said nucleic acid, said gene therapy vector and/or said cell for the treatment of tumours of the nervous system, in particular for the treatment of tumours of the cranial or peripheral nerves, tumours associated with neurofibromatosis, schwannomas, neurofibromas and malignant nerve sheath tumours.

BACKGROUND OF THE INVENTION

Neurofibromatosis (NF) is a genetic disorder, which results in a medical condition affecting the nervous system, skin, bones, and muscles and manifests itself often by the presence of multiple soft nodules, neurofibromas and is associated with hyperpigmented spots. The disease is inherited as an autosomal dominant trait. Neurofibromatosis exists in three different forms: Neurofibromatosis type 1 (NF1), known as Von Recklinghausen's disease, Neurofibromatosis type 2 (NF2), and Neurofibromatosis type 3 (NF3), often referred to schwannomatosis. The disorders occur as a result of genetic defects. The gene for NF1, has been located on chromosome 17 and for NF2, on chromosome 22. A candidate gene for schwannomatosis (NF3) is SMARCB1, which is located on chromosome 22 in proximity to the gene for NF2.

NF1, also known as von Recklinghausen Disease, is a hereditary disease with a birth incidence of one in 2500-3000. It associated a mutation of the gene Nf1 which is located on human chromosome 17q11.2 and compromises 60 exons spanning 350 kb of genomic DNA. The Nf1 gene encodes for neurofibromin 1, a tumour suppressor postulated to function in part as a Ras GTPase-activating protein and negatively regulating the Ras oncogene signal transduction pathway. Neurofibromin is expressed throughout the nervous system and negatively influences cell proliferation.

NF1 is characterized by a variety of disorders including the appearance of café-au-lait patches (skin discolorations), skin-fold freckling, Lisch nodules, plexiform neurofibromas, cutaneous neurofibromas, scoliosis, pseudo arthrosis of the tibia or renal artery stenosis. It is further associated with skeletal dysplasia, vascular dysplasia, learning disabilities, epilepsy, optic pathway glioma, cerebral glioma, seizures and other tumours of the neural crest origin, such as pheochromocytomas. NF1 may also result in malignant peripheral nerve sheath tumour (MPNST).

The occurrence of neurofibromas in NF1 especially on the spinal cord may result in secondary abnormalities of the CNS due to the exerted pressure. Cognitive impairment, multiple sclerosis and epilepsy have been associated with NF1. The most common neurological symptom in NF1 for children is a cognitive disability that is characterized by below average intelligent quotient. In NF1, neurofibromas most commonly grow on the skin or on the nerve to the eye. A tumour that grows on the nerve to the eye is commonly called an optic glioma, and if it grows large enough can cause problems with vision, including blindness. Optic pathway gliomas are frequent in younger children, but may also appear in older patients. If untreated it may lead to visual loss and or visual defects such as strabismus, proptosis, afferent pupillary defect optic disc oedema or atrophy. Chemotherapy and radiotherapy present potential treatments. They exhibit however side effects. Lisch nodules in NF1 may further affect the iris or the eyelid. Idiopathic congenital ptosis and congenital acquired glaucoma also occur in NF1.

The term neurofibroma has been coined by von Recklinghausen and refers to benign tumours. These tumours can grow anywhere in the body where there are nerve cells. This includes nerves just under the surface of the skin, as well as nerves deeper within the body, spinal cord and/or brain. Neurofibromas usually manifest in benign, focal cutaneous or subcutaneous lesions or plexiform tumours. Often neurofibromas originated from neoplastic Schwann cells, fibroblast and perineural cells, which are embedded in a collagen fibre matrix. Neurofibroma can rarely be surgically removed from the nerves without damaging the nerves. Most commonly neurofibroma occur on the skin and are highly visible. Patients suffering from neurofibroma therefore have a tendency for social isolation and may necessitate psychological care.

Moreover subjects afflicted with NF1 have a high risk of developing malignant peripheral nerve sheath tumours (MPNST). MPNST develop often from prior plexiform or focal subcutaneous neurofibroma. Due to a high probability of metastasis MPNST are particularly aggressive and have poor prospects.

NF2 is an autosomal-dominant multiple neoplasia syndrome that results from mutations in the Nf2 tumour suppressor gene. The Nf2 tumour suppressor gene is located on human chromosome 22 and comprises 17 exons. The Nf2 gene encodes for a 69 kDa product referred to as moesin-ezrin-radixin-like protein (merlin), also referred to neurofibromin 2 or schwannomin. Merlin is a membrane-cytoskeleton scaffolding protein that links the membrane or membrane glycoproteins to the actin cortex of the cells. Human merlin, which exists in two isoforms, is expressed throughout the nervous tissues and localizes at cell-cell adherens junctions. Its function as a tumour suppressor is thought to evoke from a contact-mediated inhibition of cell proliferation.

NF2, is characterized by bilateral vestibular schwannomas with associated symptoms of tinnitus, hearing loss and balance dysfunction. Other findings include schwannomas of other cranial and peripheral nerves, meningiomas and juvenile posterior subcapsular cataract.

NF3, also referred to as Schwannomatosis is a more recently described type of neurofibromatosis characterized by multiple cutaneous schwannomas, central nervous system tumours, and other neurological complications.

Schwann cell tumours, referred to as schwannomas, are nerve sheath neoplasms that appear sporadically and in association with genetic syndromes such as Schwannomatosis or Neurofibromatosis type 2 (NF2). Despite their predominantly benign nature, these tumours often have a devastating impact on patients' life quality, as treatment options are often limited to tumour resection by surgery—therein endangering long-term nerve functionality. In the hereditary tumour syndrome NF2 with an incidence of 1 in 33,000 live births (Evans et al., 2010), this often means lifelong deafness as schwannomas predominantly appear at the vestibulocochlear nerve (vestibular schwannoma). Bilateral vestibular schwannomas occur particularly often in NF2 with a frequency of 90-95% (Asthagiri et al., 2009). Moreover meningiomas are the second most common tumours associated with NF2, wherein intracranial meningiomas and intradural extramedullary spinal meningiomas are particularly frequent. Furthermore spinal cord ependymomas are associated with NF2. Most subjects afflicted with NF2 will moreover develop peripheral neuropathy, which often result from tumours comprising the function of the nervous system. Skin tumours including skin plaques, subcutaneous tumours and intradermal tumours are also associated with NF2.

The multifocality of tumours appearing during the lifetime of individuals with Nf2 gene mutations further indicates the urgent need for pharmacological therapies that enable systemic tumour control in particular in NF2 patients (Asthagiri et al., 2009).

Like for other orphan diseases, existing oncology drugs were repurposed for NF2 disease in several clinical trials over the past years (Bakker et al., 2016). So far, only the VEGF-inhibitory antibody bevacizumab showed limited efficacy for schwannoma growth control and hearing improvement (Plotkin et al., 2009); but it is accompanied by severe side effects in long-term use (Mautner et al., 2010; Slusarz et al., 2014). However, disease-targeted therapies addressing NF2-related biological specifics are currently still not available.

Neuregulin 1 (NRG1) is a trophic factor containing an epidermal growth factor (EGF)-like domain that signals by stimulating ErbB receptor tyrosine kinases (Mei and Xiong, 2008). The biological effects of NRG1 are highly versatile but its role in the peripheral nervous system (PNS) has been extensively studied in the past years. During PNS development, axonal NRG1 regulates myelin thickness by determining Schwann cell fate (Michailov et al., 2004). While the growth factor-like molecule NRG1 is dispensable for maintenance of myelin sheaths after development, it gains importance again for nerve repair processes and especially remyelination after injury (Fricker et al., 2011). Importantly, a recent publication demonstrated that myelination is not only controlled by membrane-retained NRG1 type III (Jessen and Mirsky, 2005), but also in a paracrine manner via proteolytic liberation of the EGF-like domain (Fleck et al., 2013).

Consistently, the soluble EGF-like domain of NRG1 could rescue a hypomyelination zebrafish mutant (Fleck et al., 2013) and was capable of ameliorating the phenotype of a Charcot-Marie-Tooth 1A animal model (Fledrich et al., 2014). Previously it was postulated that not only Schwann cell-intrinsic signalling cues but also extracellular factors may play a role in schwannomas (Schulz et al., 2014a). Furthermore, it was demonstrated that the axon surface molecule Neuregulin1 type III (NRG1 type III) shows reduced expression in nerves with a conditional nf2 gene knockout (Schulz et al., 2014b).

Stove et al. discusses implications of neuregulins as EGF-like ligands in the activation of human epidermal growth factor receptors (HERs) and their influence on cancer progression. WO 01/89568 A proposes the use neuregulin-2-polypeptides for treating multiple sclerosis, spinal muscular atrophy, nerve injury or Alzheimer's disease, by increasing mitogenesis, survival, growth or differentiation of cells expressing an erbB receptor that is selective for neuregulin-2. WO 01/89568 A also proposes a treatment of a glial tumor by inhibiting the proliferation of the tumor cells. The treatment involves the administration of an antibody that inhibits the binding of an NRG-2 polypeptide to a receptor present on the surface of the tumor cell.

As described herein, Neuregulin administration represents an effective therapeutic approach for treating tumours of the nervous system and associated medical conditions, in particular in relation to neurofibromatosis. The therapeutic administration of Neuregulin for the treatment of these medical conditions has not been previously described.

SUMMARY OF THE INVENTION

In light of the prior art the technical problem underlying the present invention is to provide alternative and/or improved means for the treatment of tumours of the nervous system, such as medical conditions associated with neurofibromatosis, tumours of the cranial or peripheral nerves, schwannomas, vestibular schwannomas, meningioma or malignant nerve sheath tumours.

This problem is solved by the features of the independent claims. Preferred embodiments of the present invention are provided by the dependent claims.

The invention therefore relates to a polypeptide for use as a medicament in the treatment and/or prevention of a tumour of the nervous system, wherein said polypeptide comprises or consists of an EGF-like domain of a neuregulin-1 protein. The invention also relates to a method for the treatment of a subject afflicted by a tumour of the nervous system or for the prevention and/or reduction of the risk of development of a tumour of the nervous system in a subject at risk thereof, wherein the method comprises the administration of a polypeptide comprising or consisting of an EGF-like domain of a neuregulin-1 protein to said subject.

Neuregulin proteins (NRG) belong to the family of epidermal growth factors (EGF) and comprise an EGF-like domain. In mammals the genes neuregulin 1 (NRG1), neuregulin 2 (NRG2), neuregulin 3 (NRG3) and neuregulin 4 (NRG4) encode for neuregulin proteins and comprise EGF-like domains that may be used in embodiments of the present invention.

According to a preferred embodiment of the present invention, the term neuregulin protein refers to the proteins encoded by the gene NRG1 (Gene ID 3084, http://www.ncbi.nlm.nih.gov/gene/3084). Through alternative splicing, the NRG1 gene encodes for different isoforms. In further embodiments the term neuregulin protein refers to all isoforms encoded by NRG1 as published on http://www.ncbi.nlm.nih.gov/gene/3084.

In preferred embodiments the term neuregulin protein therefore refers to the following isoforms encoded by NRG1: human pro-neuregulin-1, membrane-bound isoform HRG-beta1c (NCBI references NM_001159995.1 and NP_001153467.1), human pro-neuregulin-1, membrane-bound isoform ndf43c (NCBI references NM_001159996.1 and NP_001153468.1), human pro-neuregulin-1, membrane-bound isoform HRG-beta1b (NCBI references NM_001159999.1 and NP_001153471.1), human pro-neuregulin-1, membrane-bound isoform HRG-betald (NCBI references NM_001160001.1 and NP_001153473.1), human pro-neuregulin-1, membrane-bound isoform HRG-gamma2 (NCBI references NM_001160002.1 and NP_001153474.1), human pro-neuregulin-1, membrane-bound isoform ndf43b (NCBI references NM_001160004.1 and NP_001153476.1), human pro-neuregulin-1, membrane-bound isoform HRG-beta3b (NCBI references NM_001160005.1 and NP_001153477.1), human pro-neuregulin-1, membrane-bound isoform HRG-gamma3 (NCBI references NM_001160007.1 and NP_001153479.1), human pro-neuregulin-1, membrane-bound isoform HRG-beta2b (NCBI references NM_001160008.1 and NP_001153480.1), human pro-neuregulin-1, membrane-bound isoform HRG-gamma (NCBI references NM_004495.3 and NP_004486.2), human pro-neuregulin-1, membrane-bound isoform HRG-beta1 (NCBI references NM_013956.3 and NP_039250.2), human pro-neuregulin-1, membrane-bound isoform HRG-beta2 (NCBI references NM_013957.3 and NP_039251.2), human pro-neuregulin-1, membrane-bound isoform HRG-beta3 (NCBI references NM_013958.3 and NP_039252.2), human pro-neuregulin-1, membrane-bound isoform SMDF (NCBI references NM_013959.3 and NP_039253.1), human pro-neuregulin-1, membrane-bound isoform ndf43 (NCBI references NM_013960.3 and NP_039254.1), human pro-neuregulin-1, membrane-bound isoform GGF2 precursor (NCBI references NM_013962.2 and NP_039256.2) and human pro-neuregulin-1, membrane-bound isoform HRG-alpha (NCBI references NM_013964.3 and NP_039258.1). The use of sequence variants of neuregulin proteins that exhibit functional analogy to the unmodified human isoform is also encompassed by the present invention.

The EGF-like domain of neuregulin-1 exhibits a high therapeutic efficiency for the treatment of tumours of the nervous system. It is known that the EGF-like domain of neuregulin-1 takes part in signal transduction by stimulating the ErbB receptor tyrosine kinase ErbB2. It is particularly preferred for the invention that the polypeptide comprising the EGF-like domain is soluble. The soluble EGF-like domain of NRG1 has previously been reported to be effective in the treatment of cardiovascular diseases (Mendes et al. 2013). However its potency in the treatment of tumours or cancer in particular of tumours of the nervous system has not been suggested nor described.

It was therefore surprising that the EGF-like domain of NRG1 does effectively inhibit the growth of tumours of the nervous system. As unraveled by the inventors and demonstrated in the examples herein, the EGF-like domain of neuregulin-1 acts preferably on the tumorous cells through a differentiation inducing signal. The differentiation stage of tumours and in particular of tumours of the nervous system is strongly associated with its behaviour. In general, an immature, less differentiated tumour is more aggressive than the more differentiated counterpart. Tumours that are differentiated resemble more closely the original healthy tissue they originate from. A tumour that resembles the original tissue to a lesser extent is termed poorly differentiated, or anaplastic.

In general, and in particular for tumours of the nervous system, poorly differentiated tumour cells exhibit a higher motility and high proliferation rates. Due this properties de-differentiated tumours cells outcompete and invade the healthy surrounding tissues. An achievement of the invention is that it was recognized that the EGF-like domain of NRG1 may act as a differentiation inducer on tumour cells of the nervous system. By differentiation of the tumour cells the proliferation rate can be reduced and tumour growth efficiently stopped or even reversed.

In particular, the polypeptide comprising the EGF-like domain of neuregulin enhances the susceptibility of tumour cells of the nervous system to mitogenic signals impeding cell proliferation. Treatment of tumour cells with the polypeptide comprising the EGF-like domain of neuregulin results in reduced rates of cell division and tumour expansion. In particular for Schwann cells, polypeptides comprising the EGF-like domain of an axon surface protein NRG1, according to preferred embodiments of the invention, are particularly efficient in differentiating Schwann cells. By differentiation of the tumorous Schwann cells physiological myelinating of the nerves can be restored and abnormal growth resulting in Schwannomas can be prevented, stopped or reversed.

The differentiation of the tumour cells by the EGF-like domain of NRG1 moreover reduces the mobility of the tumour cells. For instance malignant schwannomas often arise spontaneously in adult patients or may occur with increased frequency in patients with Neurofibromatosis type I. Often these tumours exhibit a low degree of differentiation, visible by a loose tissue connection, and augmented frequency of metastasis. By treating benign neurofibromas with the polypeptide according to the invention the tumour can be contained and the development of malignant peripheral nerve sheath tumor (MPNST) as well as subsequent metastasis prevented.

Moreover, in some embodiments of the invention the polypeptide described herein is used in a preventive therapy of subjects afflicted by a risk of developing a tumour of the nervous system. Without being limited by theory, the polypeptide advantageously impedes the de-differentiation process believed to be at the origin of tumour formation. Through this approach newly developing tumours with at an early stage that do not yet result in symptoms of a disease may be efficiently prevented from developing into severe tumours. Due to the low side effects in treatments using the polypeptide according to the invention, long term therapies are possible. For a preventive approach it may even be preferred to administer the polypeptide at a regular interval over multiple weeks, months, or years without significant detrimental side effects.

In a preferred embodiment of the invention the polypeptide for use as a medicament is characterized in that the polypeptide is a soluble fragment of a neuregulin protein. A preferred embodiment of the invention therefore refers to a soluble polypeptide comprising the EGF-like domain of neuregulin. According to the invention "soluble" preferably refers to fragments of proteins or polypeptides that are not permanently membrane bound. Many isoforms of neuregulin proteins are transmembrane proteins, which are thus membrane-retained. The preferred embodiment of a soluble fragment of a neuregulin protein therefore refers preferably to fragments of a transmembrane neuregulin, which are not membrane-retained.

It is particularly preferred that the soluble fragment of a neuregulin protein refers to the extracellular domain of a neuregulin protein that comprises the EGF-like domain. The soluble EGF-like domain of neuregulin is particularly potent for the treatment of tumours of the nervous system. The preferred embodiment allows for an efficient distribution of the therapeutic polypeptide throughout the organism of a treated subject. In particular by systemic administration e.g. by intravenous injection the soluble polypeptide can be transported by the vascular system throughout the body of a treated subject. Moreover, protein clustering or precipitation can be avoided. It was particularly surprising that soluble fragments of the neuregulin protein exhibit a high tendency to localize to tumours of the nervous system. Soluble polypeptides comprising the EGF-like domain of a neuregulin protein show therefore an augmented specificity and reduced side effects. Advantageously the concentration of the polypeptide comprising the EGF-like domain may potentially be increased to high therapeutic levels without introducing unwanted side effects.

A particular preferred embodiment of a soluble fragment of a neuregulin protein is a polypeptide according to SEQ ID NO 9 as well as functional analogous polypeptides thereof. In a preferred embodiment the polypeptide has an amino acid sequence identity of at least 80%, preferably of at least 90%, to SEQ ID NO 9. These polypeptides are preferably characterised by a high stability and biocompatibility. Additionally, since the degradation rate of these peptides is expected to be relatively low, they are expected to show a prolonged therapeutically effect.

In a preferred embodiment the polypeptide for use as a medicament according to the invention is characterized in that neuregulin protein is human neuregulin1 type I, human neuregulin1 type II and/or human neuregulin1 type III, or a fragment thereof.

In a preferred embodiment of the invention the polypeptide for use as a medicament is characterized in that the polypeptide comprises or consists of an amino acid sequence according to SEQ ID NO 9-14 or an amino acid sequence with an identity of at least 80%, preferably of at least 90%, to any one of SEQ ID NO 9-14.

In a preferred embodiment of the invention the polypeptide for use as a medicament is characterized in that the polypeptide consists of an amino acid sequence according to SEQ ID NO 9 or of an amino acid sequence with an identity of at least 80%, preferably of at least 90% to SEQ ID NO 9.

The polypeptide as described herein is intended for use as a medicament in the treatment of a tumour of the nervous system, wherein the tumour is preferably a tumour of the cranial or peripheral nerves. Preferably a tumour of the cranial or peripheral nerves refers to a schwannoma, a neurofibroma, a perineurioma or a malignant nerve sheath tumour.

In one embodiment the polypeptide for use as a medicament as described herein is characterised in that the tumour to be treated is a malignant nerve sheath tumour.

In one embodiment the polypeptide for use as a medicament as described herein is characterised in that the tumour to be treated is a schwannoma.

In one embodiment the polypeptide for use as a medicament as described herein is characterised in that the tumour to be treated is a neurofibroma.

It is to be understood the preferred embodiments of the polypeptide for use as a medicament as described herein are preferably administered in the method for treating a subject or preventing/reducing risk a subject afflicted by or in risk of the development of a tumour of the nervous system.

The invention therefore encompasses a method for treating and/or preventing, or reducing the risk of development of, one or more of the tumours listed herein. In some embodiments the present invention relates to an NRG1-replacement therapy.

In one embodiment the polypeptide for use as a medicament as described herein is characterised in that treatment and/or prevention of medical conditions associated with genetic deficiency in Neurofibromatosis type 1, Neurofibromatosis type 2 and/or Neurofibromatosis type 3 is intended.

Specific examples of medical conditions that are associated with neurofibromatosis, which are preferably treated by the use of the polypeptide, the nucleic acid and/or the gene therapy vector according to the invention or preferred embodiments thereof include but are not limited to neurofibromas, plexiform neurofibromas, cutaneous neurofibroma, epilepsy, learning disabilities, optic pathway glioma as well as visual losses associated with these, cerebral glioma, seizures and other tumours of the neural crest origin, such as pheochromocytomas, malignant peripheral nerve sheath tumours, bilateral vestibular schwannomas with associated symptoms of tinnitus, hearing loss and balance dysfunction, schwannomas of other cranial and peripheral nerves, meningiomas, intracranial meningiomas, intradural extramedullary spinal meningiomas, skin tumours including skin plaques, subcutaneous tumours and intradermal tumours, ependymomas or ependymomas of the spinal cord.

It was surprising that polypeptides according to the invention and preferred embodiments thereof are efficient for treating these medical conditions associated with neurofibromatosis. The approach to administer a polypeptide comprising an EGF-like domain of a neuregulin protein according to the invention constitutes a departure of the state of the art. For example, a person skilled in the art may have attempted to treat NF1, NF2 and/or NF3 by replacing the proteins encoded by NF1 gene, NF2 gene and/or NF3 genes. For instance, a person skilled in the art may have attempted to provide exogenous merlin inside of cells of a subject afflicted by NF2. However the use of the EGF-like domain of an axon surface protein like NRG1 for the treatment of diseases associated with neurofibromatosis is an alternative and novel strategy. The strategy is surprisingly effective. The provision of an extracellular soluble polypeptide has therefore therapeutic advantages over attempts to replace the NF gene encoded proteins inside of the cells as e.g. merlin inside of Schwann cells in NF2 patients. In particular the therapeutically effective dosage of the polypeptides can be more easily and securely controlled and side effects can be minimized.

In a further preferred embodiment the invention relates to a nucleic acid molecule for use as a medicament in the treatment and/or prevention of a tumour of the nervous system, wherein the nucleic acid molecule encodes a polypeptide according to the invention. The invention therefore also relates in a further preferred embodiment to a method for treating a subject afflicted by or in risk of the development of a tumour of the nervous system, wherein the method comprises the administration of a nucleic acid molecule encoding a polypeptide according to the invention or preferred embodiments thereof.

In a preferred embodiment the nucleic acid molecule is used for the treatment and/or prevention a tumour of the cranial or peripheral nerves. In a preferred embodiment the nucleic acid molecule is used for the treatment and/or prevention a malignant nerve sheath tumour. In a preferred embodiment the nucleic acid molecule is used for the treatment and/or prevention a schwannoma. In a preferred embodiment the nucleic acid molecule is used for the treatment and/or prevention a neurofibroma. In a preferred embodiment the nucleic acid molecule is used for the treatment and/or prevention of tumours associated with genetic deficiency in neurofibromatosis type 1, neurofibromatosis type 2 and/or neurofibromatosis type 3.

In a further preferred embodiment the invention relates to a gene therapy vector for use as a medicament in the treatment and/or prevention of a tumour of a nervous system comprising said nucleic acid molecule or preferred embodiments thereof. In this further preferred embodiment the invention thus also relates to a method for treating a subject afflicted by or in risk of the development of a tumour of the nervous system, wherein the method comprises the administration of gene therapy vector comprising said nucleic acid molecule or preferred embodiments thereof.

In a preferred embodiment the gene therapy vector is used for the treatment and/or prevention tumour of the cranial or peripheral nerves, a malignant nerve sheath tumour, a schwannoma and/or a neurofibroma.

In particularly preferred embodiments the gene therapy vector is used for the treatment and/or prevention of tumours associated with genetic deficiency in neurofibromatosis type 1, neurofibromatosis type 2 and/or neurofibromatosis type 3.

DETAILED DESCRIPTION OF THE INVENTION

In Table 1 the nucleotide sequence of preferred embodiments of neuregulins are listed.

TABLE 1

| Nucleotide sequences of preferred neuregulin proteins | |
|---|---|
| SEQ ID NO 1: DNA sequence of human neuregulin (NRG1), transcript variant HRG-beta1c; CDS (92-1915) of NCBI reference sequence NM_001159995.1 | ATGGGGAAAGGACGCGCGGGCCGAGTTGGCACCACAGCCTT<br>GCCTCCCCGATTGAAAGAGATGAAAAGCCAGGAATCGGCTGC<br>AGGTTCCAAACTAGTCCTTCGGTGTGAAACCAGTTCTGAATAC<br>TCCTCTCTCAGATTCAAGTGGTTCAAGAATGGGAATGAATTGA<br>ATCGAAAAAACAAACCACAAAATATCAAGATACAAAAAAAGCC<br>AGGGAAGTCAGAACTTCGCATTAACAAAGCATCACTGGCTGAT<br>TCTGGAGAGTATATGTGCAAAGTGATCAGCAAATTAGGAAATG<br>ACAGTGCCTCTGCCAATATCACCATCGTGGAATCAAACGAGAT<br>CATCACTGGTATGCCAGCCTCAACTGAAGGAGCATATGTGTCT<br>TCAGCTACATCTACATCCACCACTGGGACAAGCCATCTTGTAA<br>AATGTGCGGAGAAGGAGAAAACTTTCTGTGTGAATGGAGGGG<br>AGTGCTTCATGGTGAAAGACCTTTCAAACCCCTCGAGATACTT<br>GTGCAAGTGCCCAAATGAGTTTACTGGTGATCGCTGCCAAAA<br>CTACGTAATGGCCAGCTTCTACAAGCATCTTGGGATTGAATTT<br>ATGGAGGCGGAGGAGCTGTACCAGAAGAGAGTGCTGACCATA<br>ACCGGCATCTGCATCGCCCTCCTTGTGGTCGGCATCATGTGT<br>GTGGTGGCCTACTGCAAAACCAAGAAACAGCGGAAAAAGCTG<br>CATGACCGTCTTCGGCAGAGCCTTCGGTCTGAACGAAACAAT<br>ATGATGAACATTGCCAATGGGCCTCACCATCCTAACCCACCCC<br>CCGAGAATGTCCAGCTGGTGAATCAATACGTATCTAAAAACGT<br>CATCTCCAGTGAGCATATTGTTGAGAGAGAAGCAGAGACATC<br>CTTTTCCACCAGTCACTATACTTCCACAGCCCATCACTCCACT<br>ACTGTCACCCAGACTCCTAGCCACAGCTGGAGCAACGGACAC<br>ACTGAAAGCATCCTTTCCGAAAGCCACTCTGTAATCGTGATGT<br>CATCCGTAGAAAACAGTAGGCACAGCAGCCCAACTGGGGGCC<br>CAAGAGGACGTCTTAATGGCACAGGAGGCCCTCGTGAATGTA<br>ACAGCTTCCTCAGGCATGCCAGAGAAACCCCTGATTCCTACC<br>GAGACTCTCCTCATAGTGAAAGGTATGTGTCAGCCATGACCAC<br>CCCGGCTCGTATGTCACCTGTAGATTTCCACACGCCAAGCTC<br>CCCCAAATCGCCCCCTTCGGAAATGTCTCCACCCGTGTCCAG<br>CATGACGGTGTCCATGCCTTCCATGGCGGTCAGCCCCTTCAT<br>GGAAGAAGAGAGACCTCTACTTCTCGTGACACCACCAAGGCT<br>GCGGGAGAAGAAGTTTGACCATCACCCTCAGCAGTTCAGCTC<br>CTTCCACCACAACCCCGCGCATGACAGTAACAGCCTCCCTGC<br>TAGCCCCTTGAGGATAGTGGAGGATGAGGAGTATGAAACGAC<br>CCAAGAGTACGAGCCAGCCCAAGAGCCTGTTAAGAAACTCGC<br>CAATAGCCGGCGGGCCAAAAGAACCAAGCCCAATGGCCACAT<br>TGCTAACAGATTGGAAGTGGACAGCAACACAAGCTCCCAGAG<br>CAGTAACTCAGAGAGTGAAACAGAAGATGAAAGAGTAGGTGA<br>AGATACGCCTTTCCTGGGCATACAGAACCCCCTGGCAGCCAG<br>TCTTGAGGCAACACCTGCCTTCCGCCTGGCTGACAGCAGGAC<br>TAACCCAGCAGGCCGCTTCTCGACACAGGAAGAAATCCAGGC<br>CAGGCTGTCTAGTGTAATTGCTAACCAAGACCCTATTGCTGTA<br>TAA |
| SEQ ID NO 2: DNA sequence of human neuregulin (NRG1), transcript variant HRG-beta1b; CDS (92-1966) of NCBI reference sequence NM_001159999.1 | ATGGGGAAAGGACGCGCGGGCCGAGTTGGCACCACAGCCTT<br>GCCTCCCCGATTGAAAGAGATGAAAAGCCAGGAATCGGCTGC<br>AGGTTCCAAACTAGTCCTTCGGTGTGAAACCAGTTCTGAATAC<br>TCCTCTCTCAGATTCAAGTGGTTCAAGAATGGGAATGAATTGA<br>ATCGAAAAAACAAACCACAAAATATCAAGATACAAAAAAAGCC<br>AGGGAAGTCAGAACTTCGCATTAACAAAGCATCACTGGCTGAT<br>TCTGGAGAGTATATGTGCAAAGTGATCAGCAAATTAGGAAATG<br>ACAGTGCCTCTGCCAATATCACCATCGTGGAATCAAACGAGAT<br>CATCACTGGTATGCCAGCCTCAACTGAAGGAGCATATGTGTCT<br>TCAGAGTCTCCCATTAGAATATCAGTATCCACAGAAGGAGCAA<br>ATACTTCTTCATCTACATCTACATCCACCACTGGGACAAGCCA<br>TCTTGTAAAATGTGCGGAGAAGGAGAAAACTTTCTGTGTGAAT<br>GGAGGGGAGTGCTTCATGGTGAAAGACCTTTCAAACCCCTCG<br>AGATACTTGTGCAAGTGCCCAAATGAGTTTACTGGTGATCGCT<br>GCCAAAACTACGTAATGGCCAGCTTCTACAAGCATCTTGGGAT<br>TGAATTTATGGAGGCGGAGGAGCTGTACCAGAAGAGAGTGCT<br>GACCATAACCGGCATCTGCATCGCCCTCCTTGTGGTCGGCAT<br>CATGTGTGTGGTGGCCTACTGCAAAACCAAGAAACAGCGGAA<br>AAAGCTGCATGACCGTCTTCGGCAGAGCCTTCGGTCTGAACG<br>AAACAATATGATGAACATTGCCAATGGGCCTCACCATCCTAAC<br>CCACCCCCCGAGAATGTCCAGCTGGTGAATCAATACGTATCTA<br>AAAACGTCATCTCCAGTGAGCATATTGTTGAGAGAGAAGCAGA<br>GACATCCTTTTCCACCAGTCACTATACTTCCACAGCCCATCAC<br>TCCACTACTGTCACCCAGACTCCTAGCCACAGCTGGAGCAAC<br>GGACACACTGAAAGCATCCTTTCCGAAAGCCACTCTGTAATCG<br>TGATGTCATCCGTAGAAAACAGTAGGCACAGCAGCCCAACTG<br>GGGGCCCAAGAGGACGTCTTAATGGCACAGGAGGCCCTCGT<br>GAATGTAACAGCTTCCTCAGGCATGCCAGAGAAACCCCTGATT<br>CCTACCGAGACTCTCCTCATAGTGAAAGGTATGTGTCAGCCAT<br>GACCACCCCGGCTCGTATGTCACCTGTAGATTTCCACACGCC<br>AAGCTCCCCCAAATCGCCCCCTTCGGAAATGTCTCCACCCGT<br>GTCCAGCATGACGGTGTCCATGCCTTCCATGGCGGTCAGCCC<br>CTTCATGGAAGAAGAGAGACCTCTACTTCTCGTGACACCACCA |

TABLE 1-continued

| Nucleotide sequences of preferred neuregulin proteins | |
|---|---|
| | AGGCTGCGGGAGAAGAAGTTTGACCATCACCCTCAGCAGTTC<br>AGCTCCTTCCACCACAACCCCGCGCATGACAGTAACAGCCTC<br>CCTGCTAGCCCCTTGAGGATAGTGGAGGATGAGGAGTATGAA<br>ACGACCCAAGAGTACGAGCCAGCCCAAGAGCCTGTTAAGAAA<br>CTCGCCAATAGCCGGCGGGCCAAAAGAACCAAGCCCAATGG<br>CCACATTGCTAACAGATTGGAAGTGGACAGCAACACAAGCTC<br>CCAGAGCAGTAACTCAGAGAGTGAAACAGAAGATGAAAGAGT<br>AGGTGAAGATACGCCTTTCCTGGGCATACAGAACCCCCTGGC<br>AGCCAGTCTTGAGGCAACACCTGCCTTCCGCCTGGCTGACAG<br>CAGGACTAACCCAGCAGGCCGCTTCTCGACACAGGAAGAAAT<br>CCAGGCCAGGCTGTCTAGTGTAATTGCTAACCAAGACCCTATT<br>GCTGTATAA |
| SEQ ID NO 3: DNA sequence of human pro-neuregulin-1, membrane-bound isoform HRG-alpha; CDS (518-2440) of NCBI reference sequence NM_013964.3 | ATGTCCGAGCGCAAAGAAGGCAGAGGCAAAGGGAAGGGCAA<br>GAAGAAGGAGCGAGGCTCCGGCAAGAAGCCGGAGTCCGCGG<br>CGGGCAGCCAGAGCCCAGCCTTGCCTCCCCGATTGAAAGAG<br>ATGAAAAGCCAGGAATCGGCTGCAGGTTCCAAACTAGTCCTT<br>CGGTGTGAAACCAGTTCTGAATACTCCTCTCTCAGATTCAAGT<br>GGTTCAAGAATGGGAATGAATTGAATCGAAAAAACAAACCACA<br>AAATATCAAGATACAAAAAAAGCCAGGGAAGTCAGAACTTCGC<br>ATTAACAAAGCATCACTGGCTGATTCTGGAGAGTATATGTGCA<br>AAGTGATCAGCAAATTAGGAAATGACAGTGCCTCTGCCAATAT<br>CACCATCGTGGAATCAAACGAGATCATCACTGGTATGCCAGC<br>CTCAACTGAAGGAGCATATGTGTCTTCAGAGTCTCCCATTAGA<br>ATATCAGTATCCACAGAAGGAGCAAATACTTCTTCATCTACATC<br>TACATCCACCACTGGGACAAGCCATCTTGTAAAATGTGCGGA<br>GAAGGAGAAAACTTTCTGTGTGAATGGAGGGGAGTGCTTCAT<br>GGTGAAAGACCTTTCAAACCCCTCGAGATACTTGTGCAAGTGC<br>CAACCTGGATTCACTGGAGCAAGATGTACTGAGAATGTGCCC<br>ATGAAAGTCCAAAACCAAGAAAAGGCGGAGGAGCTGTACCAG<br>AAGAGAGTGCTGACCATAACCGGCATCTGCATCGCCCTCCTT<br>GTGGTCGGCATCATGTGTGTGGTGGCCTACTGCAAAACCAAG<br>AAACAGCGGAAAAAGCTGCATGACCGTCTTCGGCAGAGCCTT<br>CGGTCTGAACGAAACAATATGATGAACATTGCCAATGGGCCTC<br>ACCATCCTAACCCACCCCCCGAGAATGTCCAGCTGGTGAATC<br>AATACGTATCTAAAAACGTCATCTCCAGTGAGCATATTGTTGA<br>GAGAGAAGCAGAGACATCCTTTTCCACCAGTCACTATACTTCC<br>ACAGCCCATCACTCCACTACTGTCACCCAGACTCCTAGCCACA<br>GCTGGAGCAACGGACACACTGAAAGCATCCTTTCCGAAAGCC<br>ACTCTGTAATCGTGATGTCATCCGTAGAAAACAGTAGGCACAG<br>CAGCCCAACTGGGGGCCCAAGAGGACGTCTTAATGGCACAG<br>GAGGCCCTCGTGAATGTAACAGCTTCCTCAGGCATGCCAGAG<br>AAACCCCTGATTCCTACCGAGACTCTCCTCATAGTGAAAGGTA<br>TGTGTCAGCCATGACCACCCCGGCTCGTATGTCACCTGTAGA<br>TTTCCACACGCCAAGCTCCCCCAAATCGCCCCCTTCGGAAAT<br>GTCTCCACCCGTGTCCAGCATGACGGTGTCCATGCCTTCCAT<br>GGCGGTCAGCCCCTTCATGGAAGAAGAGAGACCTCTACTTCT<br>CGTGACACCACCAAGGCTGCGGGAGAAGAAGTTTGACCATCA<br>CCCTCAGCAGTTCAGCTCCTTCCACCACAACCCCGCGCATGA<br>CAGTAACAGCCTCCCTGCTAGCCCCTTGAGGATAGTGGAGGA<br>TGAGGAGTATGAAACGACCCAAGAGTACGAGCCAGCCCAAGA<br>GCCTGTTAAGAAACTCGCCAATAGCCGGCGGGCCAAAAGAAC<br>CAAGCCCAATGGCCACATTGCTAACAGATTGGAAGTGGACAG<br>CAACACAAGCTCCCAGAGCAGTAACTCAGAGAGTGAAACAGA<br>AGATGAAAGAGTAGGTGAAGATACGCCTTTCCTGGGCATACA<br>GAACCCCCTGGCAGCCAGTCTTGAGGCAACACCTGCCTTCCG<br>CCTGGCTGACAGCAGGACTAACCCAGCAGGCCGCTTCTCGAC<br>ACAGGAAGAAATCCAGGCCAGGCTGTCTAGTGTAATTGCTAA<br>CCAAGACCCTATTGCTGTATAA |
| SEQ ID NO 4: DNA sequence of human pro-neuregulin-1, membrane-bound isoform HRG-gamma; CDS (518-1153) of NCBI reference sequence NM_004495.3 | ATGTCCGAGCGCAAAGAAGGCAGAGGCAAAGGGAAGGGCAA<br>GAAGAAGGAGCGAGGCTCCGGCAAGAAGCCGGAGTCCGCGG<br>CGGGCAGCCAGAGCCCAGCCTTGCCTCCCCGATTGAAAGAG<br>ATGAAAAGCCAGGAATCGGCTGCAGGTTCCAAACTAGTCCTT<br>CGGTGTGAAACCAGTTCTGAATACTCCTCTCTCAGATTCAAGT<br>GGTTCAAGAATGGGAATGAATTGAATCGAAAAAACAAACCACA<br>AAATATCAAGATACAAAAAAAGCCAGGGAAGTCAGAACTTCGC<br>ATTAACAAAGCATCACTGGCTGATTCTGGAGAGTATATGTGCA<br>AAGTGATCAGCAAATTAGGAAATGACAGTGCCTCTGCCAATAT<br>CACCATCGTGGAATCAAACGAGATCATCACTGGTATGCCAGC<br>CTCAACTGAAGGAGCATATGTGTCTTCAGAGTCTCCCATTAGA<br>ATATCAGTATCCACAGAAGGAGCAAATACTTCTTCATCTACATC<br>TACATCCACCACTGGGACAAGCCATCTTGTAAAATGTGCGGA<br>GAAGGAGAAAACTTTCTGTGTGAATGGAGGGGAGTGCTTCAT<br>GGTGAAAGACCTTTCAAACCCCTCGAGATACTTGTGCAAGTAA |

In one embodiment the invention therefore encompasses a nucleic acid molecule, and various uses thereof as described herein, selected from the group consisting of:

a) a nucleic acid molecule comprising or consisting of a nucleotide sequence that encodes an EGF-like domain of a neuregulin protein, preferably an EGF-like domain of a sequence according to SEQ ID NO 1-4, b) a nucleic acid molecule comprising or consisting of a nucleotide sequence that encodes an EGF-like domain of a neuregulin protein, preferably the EGF-like domain of a sequence according to SEQ ID NO 1-4, wherein the length of the nucleic acid molecule is in between 50 and 500 nucleic acids preferably between 100 and 300 nucleic acids, most preferably between 150 and 220 nucleic acids, wherein the surrounding sequences are preferably provided as neuregulin-encoding nucleotide sequences flanking the EGF-like domain, c) a nucleic acid molecule which is complementary to a nucleotide sequence in accordance with a) or b);

d) a nucleic acid molecule comprising a nucleotide sequence having sufficient sequence identity to be functionally analogous/equivalent to a nucleotide sequence according to a), b) or c), comprising preferably a sequence identity to a nucleotide sequence according to a) or b) of at least 70%, 80%, preferably 90%, more preferably 95%;

e) a nucleic acid molecule which, as a consequence of the genetic code, is degenerated into a nucleotide sequence according to a) through d); and f) a nucleic acid molecule according to a nucleotide sequence of a) through e) which is modified by deletions, additions, substitutions, translocations, inversions and/or insertions and functionally analogous/equivalent to a nucleotide sequence according to a) through d).

Further sequence variants are hereby incorporated in the invention that exhibit an alternative nucleic acid sequence to SEQ ID NO 1-4 but encode the same or a corresponding or functionally analogous amino acid sequence. Sequence variants obtained via using degeneracy of the genetic code are included. Sequence optimized nucleic acid sequences of those sequences provided herein are also included within the scope of the invention.

Amino acid sequences of preferred neuregulin proteins are listed under Table 2.

TABLE 2

| Amino acid sequences of preferred neuregulin proteins | |
|---|---|
| SEQ ID NO 5: Amino acid sequence of human neuregulin (NRG1), transcript variant HRG-beta1c;<br>NCBI Reference Sequence: NP_001153467.1<br>The EGF-like domain has been underlined | MGKGRAGRVGTTALPPRLKEMKSQESAAGSKLVLRCETSSEYS<br>SLRFKWFKNGNELNRKNKPQNIKIQKKPGKSELRINKASLADSGE<br>YMCKVISKLGNDSASANITIVESNEIITGMPASTEGAYVSSATSTS<br>TTGTSHLVKCAEKEKTFCVNGGECFMVKDLSNPSRYLCKCPNEF<br>TGDRCQNYVMASFYKHLGIEFMEAEELYQKRVLTITGICIALLVVG<br>IMCVVAYCKTKKQRKKLHDRLRQSLRSERNNMMNIANGPHHPN<br>PPPENVQLVNQYVSKNVISSEHIVEREAETSFSTSHYTSTAHHST<br>TVTQTPSHSWSNGHTESILSESHSVIVMSSVENSRHSSPTGGPR<br>GRLNGTGGPRECNSFLRHARETPDSYRDSPHSERYVSAMTTPA<br>RMSPVDFHTPSSPKSPPSEMSPPVSSMTVSMPSMAVSPFMEEE<br>RPLLLVTPPRLREKKFDHHPQQFSSFHHNPAHDSNSLPASPLRIV<br>EDEEYETTQEYEPAQEPVKKLANSRRAKRTKPNGHIANRLEVDS<br>NTSSQSSNSESETEDERVGEDTPFLGIQNPLAASLEATPAFRLAD<br>SRTNPAGRFSTQEEIQARLSSVIANQDPIAV |
| SEQ ID NO 6: Amino acid sequence of human pro-neuregulin-1, membrane-bound isoform HRG-beta1b;<br>NCBI Reference Sequence: NP_001153471.1<br>The EGF-like domain has been underlined | MGKGRAGRVGTTALPPRLKEMKSQESAAGSKLVLRCETSSEYS<br>SLRFKWFKNGNELNRKNKPQNIKIQKKPGKSELRINKASLADSGE<br>YMCKVISKLGNDSASANITIVESNEIITGMPASTEGAYVSSESPIRI<br>SVSTEGANTSSSTSTSTTGTSHLVKCAEKEKTFCVNGGECFMVK<br>DLSNPSRYLCKCPNEFTGDRCQNYVMASFYKHLGIEFMEAEELY<br>QKRVLTITGICIALLVVGIMCVVAYCKTKKQRKKLHDRLRQSLRSE<br>RNNMMNIANGPHHPNPPPENVQLVNQYVSKNVISSEHIVEREAE<br>TSFSTSHYTSTAHHSTTVTQTPSHSWSNGHTESILSESHSVIVMS<br>SVENSRHSSPTGGPRGRLNGTGGPRECNSFLRHARETPDSYRD<br>SPHSERYVSAMTTPARMSPVDFHTPSSPKSPPSEMSPPVSSMT<br>VSMPSMAVSPFMEEERPLLLVTPPRLREKKFDHHPQQFSSFHHN<br>PAHDSNSLPASPLRIVEDEEYETTQEYEPAQEPVKKLANSRRAK<br>RTKPNGHIANRLEVDSNTSSQSSNSESETEDERVGEDTPFLGIQ<br>NPLAASLEATPAFRLADSRTNPAGRFSTQEEIQARLSSVIANQDPI<br>AV |
| SEQ ID NO 7: Amino acid sequence of human pro-neuregulin-1, membrane-bound isoform HRG-alpha<br>NCBI Reference Sequence: NP_039258.1<br>The EGF-like domain has been underlined | MSERKEGRGKGKGKKKERGSGKKPESAAGSQSPALPPRLKEM<br>KSQESAAGSKLVLRCETSSEYSSLRFKWFKNGNELNRKNKPQNI<br>KIQKKPGKSELRINKASLADSGEYMCKVISKLGNDSASANITIVES<br>NEIITGMPASTEGAYVSSESPIRISVSTEGANTSSSTSTSTTGTSH<br>LVKCAEKEKTFCVNGGECFMVKDLSNPSRYLCKCQPGFTGARC<br>TENVPMKVQNQEKAEELYQKRVLTITGICIALLVVGIMCVVAYCKT<br>KKQRKKLHDRLRQSLRSERNNMMNIANGPHHPNPPPENVQLVN<br>QYVSKNVISSEHIVEREAETSFSTSHYTSTAHHSTTVTQTPSHSW<br>SNGHTESILSESHSVIVMSSVENSRHSSPTGGPRGRLNGTGGPR<br>ECNSFLRHARETPDSYRDSPHSERYVSAMTTPARMSPVDFHTP<br>SSPKSPPSEMSPPVSSMTVSMPSMAVSPFMEEERPLLLVTPPRL<br>REKKFDHHPQQFSSFHHNPAHDSNSLPASPLRIVEDEEYETTQE<br>YEPAQEPVKKLANSRRAKRTKPNGHIANRLEVDSNTSSQSSNSE<br>SETEDERVGEDTPFLGIQNPLAASLEATPAFRLADSRTNPAGRFS<br>TQEEIQARLSSVIANQDPIAV |

TABLE 2-continued

| Amino acid sequences of preferred neuregulin proteins | |
|---|---|
| SEQ ID NO 8: Human pro-neuregulin-1, membrane-bound isoform HRG-gamma comprising an EGF-like domain (underlined) NCBI Reference Sequence: NP_004486.2 | MSERKEGRGKGKGKKKERGSGKKPESAAGSQSPALPPRLKEM KSQESAAGSKLVLRCETSSEYSSLRFKWFKNGNELNRKNKPQNI KIQKKPGKSELRINKASLADSGEYMCKVISKLGNDSASANITIVES NEIITGMPASTEGAYVSSESPIRISVSTEGANTSSSTSTSTTGT<u>SH LVKCAEKEKTFCVNGGECFMVKDLSNPSRYLCK</u> |

In one embodiment the invention therefore encompasses a polypeptide as described herein comprising or consisting of an amino acid sequence selected from the group consisting of:

a) an amino acid sequence comprising or consisting of the EGF-like domain of a neuregulin protein, preferably the EGF-like domain of an amino acid sequence according to SEQ ID NO 5-8, b) an amino acid sequence comprising or consisting of the EGF-like domain of a neuregulin protein, preferably the EGF-like domain of an amino acid sequence according to SEQ ID NO 5-8, wherein the length of the amino acid molecule is in between 25 and 150 amino acids preferably between 40 and 100 amino acids, most preferably between 50 and 70 amino acids, wherein the surrounding sequences are preferably provided as neuregulin protein sequences flanking the EGF-like domain, c) an amino acid sequence having sufficient sequence identity to be functionally analogous/equivalent to an amino acid sequence according to a), comprising preferably a sequence identity to an amino acid sequence according to a) of at least 70%, 80%, preferably 90%, more preferably 95%; and d) an amino acid sequence of a), b) or c) which is modified by deletions, additions, substitutions, translocations, inversions and/or insertions and functionally analogous/equivalent to an amino acid sequence according to a), b) or c).

The amino acid sequence of particularly preferred embodiments comprising the EGF-like domain of neuregulins as encompassed by the invention are listed in Table 3:

TABLE 3

| Preferred polypeptides comprising the EGF-like domains of a neuregulin protein | |
|---|---|
| SEQ ID NO 9: Amino acid sequence of recombinant human neuregulin-1 beta EGF domain (rhNGR1) Obtainable from transcript variant HRG-beta1c; NP_001153467.1 | SHLVKCAEKEKTFCVNGGECFM VKDLSNPSRYLCKCPNEFTGD RCQNYVMASFYKHLGIEF |
| SEQ ID NO 10: amino acid sequence of the EGF-like domain of human pro-neuregulin-1, membrane-bound isoform HRG-alpha; NP_039258.1 | SHLVKCAEKEKTFCVNGGECFM VKDLSNPSRYLCKCQPGFTGA RCT |
| SEQ ID NO 11: amino acid sequence of the EGF-like domain of human neuregulin-1, membrane-bound isoform HRG-gamma; NP_004486.2 | SHLVKCAEKEKTFCVNGGECFM VKDLSNPSRYLCK |

TABLE 3-continued

| Preferred polypeptides comprising the EGF-like domains of a neuregulin protein | |
|---|---|
| SEQ ID NO 12: | CVNGGECFMVKDLSNPSRYLCK CPNEFTGDRCQ |
| SEQ ID NO 13: | CVNGGECFMVKDLSNPSRYLCK CQPGFTGARCT |
| SEQ ID NO 14: | CVNGGECFMVKDLSNPSRYLCK |

According to the present invention the term "EGF-like domain of a neuregulin protein" encompasses the sequences identified under SEQ ID NO 9-14, including sequence variants thereof such as are described herein, and functionally analogous sequences.

In some embodiments the "EGF-like domain of a neuregulin protein" preferably refers to a polypeptide encoded by the neuregulin gene that binds to and activates ErbB2, ErbB3, ErbB4 or combinations thereof and bears a structural and/or sequence similarity to the polypeptide according to SEQ ID NO 9. The term "EGF-like domain of a neuregulin protein" therefore also encompasses any protein sequences with essentially the same or similar activity as SEQ ID NO 9, when tested for the binding to and activation of ErbB2, ErbB3 or ErbB4, wherein essentially the same or similar activity relates to at least 5%, preferably 10, 20, 30, 50 or more preferably at least 70% of the activity of SEQ ID NO 9.

A preferred embodiment of the invention therefore encompasses a polypeptide as described herein comprising or consisting of an amino acid sequence selected from the group consisting of:

a) an amino acid sequence according to SEQ ID NO 9-14 b) an amino acid sequence according to a) that comprises a 0 to 10 amino acid addition or deletion at the N and/or C terminus, c) an amino acid sequence comprising an amino acid sequence according to to a) or b), wherein the length of the amino acid sequence is in between 25 and 150 amino acids preferably between 40 and 100 amino acids, most preferably between 50 and 70 amino acids, amino acids, wherein the surrounding sequences are preferably provided as neuregulin protein sequences flanking the EGF-like domain, such as derived from SEQ ID NO 5-8, d) an amino acid sequence having sufficient sequence identity to be functionally analogous/equivalent to an amino acid sequence according to a), b) or c), comprising preferably a sequence identity to an amino acid sequence according to a) of at least 70%, 80%, preferably 90%, more preferably 95%; and e) an amino acid molecule according to an amino acid sequence of a), b), c) or d) which is modified by deletions, additions, substitutions, translocations, inversions and/or insertions and functionally analogous/equivalent to an amino acid sequence according to a), b), c) or d).

Functionally analogous sequences refer preferably to the ability to encode a functional peptide comprising the EGF-like domain.

Protein modifications to the polypeptide comprising the EGF-like domain, which may occur through substitutions in amino acid sequence, and nucleic acid sequences encoding such molecules, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein. In some embodiments this amendment will not significantly alter the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, lie and Leu; the non-polar aromatic amino acids Phe, Trp and Tyr; the neutral polar amino acids Ser, Thr, Cys, Gin, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

The present invention encompasses gene therapy comprising the administration of a therapeutic gene encoding the neuregulins and EGF-like domains described herein.

The term gene therapy preferably refers to the transfer of DNA into a subject in order to treat a disease. The person skilled in the art knows strategies to perform gene therapy using gene therapy vectors. Such gene therapy vectors are optimized to deliver foreign DNA into the host cells of the subject. In a preferred embodiment the gene therapy vectors may be a viral vector.

Viruses have naturally developed strategies to incorporate DNA in to the genome of host cells and may therefore be advantageously used. Preferred viral gene therapy vectors may include but are not limited to retroviral vectors such as moloney murine leukemia virus (MMLV), adenoviral vectors, lentiviral, adenovirus-associated viral (AAV) vectors, pox virus vectors, herpes simplex virus vectors or human immunodeficiency virus vectors (HIV-1). However also non-viral vectors may be preferably used for the gene therapy such as plasmid DNA expression vectors driven by eukaryotic promoters or liposomes encapsulating the transfer DNA. Furthermore preferred gene therapy vectors may also refer to methods to transfer of the DNA such as electroporation or direct injection of nucleic acids into the subject. Moreover it may be preferred that the gene therapy vectors for example a viral gene therapy vector is adapted to target tumour cells and in particular tumour cells of the nervous system. To this end the viral capsid may be conjugated with ligands binding to tumour cells such as epidermal growth factors, basic fibroblast growth vectors or monoclonal antibodies. It may also be preferred that the viral gene therapy vectors are genetically modified using tumour specific promoters to enhance the expression of the nucleic acid specifically within the tumour cells. Preferred gene therapy vectors may therefore comprise vectors for an inducible or conditional expression of the polypeptides. The person skilled in the art knows how to choose preferred gene therapy vectors according the need of application as well as the methods on how to implement the nucleic acid into the gene therapy vector. (P. Seth et al., 2005, N. Koostra et, al. 2009, W. Walther et al. 2000, Waehler et al. 2007)

The nucleic acid according to the invention and preferred embodiments thereof, in particular a nucleic acid encoding for a polypeptide according to SEQ ID 9, is particularly efficient for gene therapy due to a high therapeutic potential at a small size. This ensures a stable integration at high expression levels over extended periods of times. The preferred embodiment of the gene therapy vector is not only efficient for the treatment of tumours of the nervous system, but also for an effective prevention of an outbreak of a tumour of the nervous system. It may therefore be particularly preferred to use the gene therapy vector as a preventive treatment for subjects afflicted by a genetic deficiency in neurofibromatosis type 1, neurofibromatosis type 2 and/or neurofibromatosis type 3.

In a further preferred embodiment the invention relates to a cell for use as a medicament in the treatment and/or prevention of a tumour of the nervous system as described herein, wherein the cell is genetically modified and comprises an exogenous nucleic acid region encoding for a polypeptide according to the invention or preferred embodiments thereof and wherein the exogenous nucleic acid region is operably linked to a promoter.

The person skilled in the art knows how to genetically modify cells in order to express the polypeptides according to the inventions. Advantageously by expressing the therapeutically effective polypeptides the cells may act as bio pump or drug factory that continuously expresses and provides the polypeptides to the subject. Thereby the amount of the polypeptides can be held at a therapeutic level over long periods. The person skilled in the art knows which cells may be preferably used to this end. In a preferred embodiment the cells are stem cells, characterized by a stable expression of the polypeptides. Stem cells may include but are not limited to, embryonic stem cells such as early embryonic stem cells and blastocyst embryonic stem cells; fetal stem cells; umbilical cord stem cells; and adult stem cells such as mesenchymal stem cells, hematopoietic stem cells, endothelial stem cells, peripheral blood stem cells, and multipotent somatic stem cells.

The cells may migrate to the site of the tumour in order to locally express the polypeptides in vicinity of the tumour. Advantageously the cells may however also be transplanted at a different location as the polypeptides can also be transported by the vascular system throughout the body of the subject. Local administration of the cells e.g. by a subcutaneous injection may therefore contribute in a systemic manner largely irrespective of the location of the cells within the body of the subject.

In a further preferred embodiment the cells for use as a medicament as described herein is characterised by introducing a therapeutically effective number of said cells to a subject within a biocompatible matrix. Preferred materials for the biocompatible matrix are agarose, carrageenan, alginate, chitosan, gellan gum, hyaluronic acid, collagen, cellulose and its derivatives, gelatin, elastin, epoxy resin, photo cross-linkable resins, polyacrylamide, polyester, polystyrene and polyurethane or polyethylene glycol (PEG). It is further preferred that the biocompatible matrix is a semi-permeable hydrogel matrix and the cells are entrapped by said matrix. Advantageously the biocompatible matrix allows for an efficient diffusion of nutrients, oxygens and other biomolecules to ensure a long lasting viability of the cells expressing the polypeptide, while immobilizing the cells. Thereby the cells can be concentrated at preferred locations within the subject. For instance the cells can be transplanted subcutaneously and/or in proximity of diseased regions of the subject i.e. close to a vestibular schwannoma. It is surprising that by introducing encapsulated cells, the cells function particularly efficiently as bio pumps and provide a high level of therapeutic polypeptides to the subject.

In a preferred embodiment the invention further relate to pharmaceutical composition for use as a medicament in the treatment and/or prevention of a tumour of the nervous system as described herein, wherein the pharmaceutical composition comprises the polypeptide, the nucleic acid, the gene therapy vector and/or the cell, and optionally a pharmaceutically accepted carrier. Preferably the pharmaceutical composition is administered to the subject at a therapeutically effective amount at any administration route as described herein.

In a preferred embodiment the pharmaceutical composition for use as a medicament as described herein is administered by introducing a therapeutically effective amount of the composition into the blood stream of a subject. This route of administration is particularly advantageous for an administration of the polypeptides. Advantageously the polypeptides and in particular the soluble polypeptides as described herein can cross the blood-brain barrier. Therefore a systemic administration by introducing a therapeutically effective amount of the polypeptides into the vascular system may be used to treat tumours of the nervous system throughout the body of the subject including the brain.

In a further preferred embodiment the pharmaceutical composition for use as a medicament as described herein is administered locally. It is particularly preferred that the pharmaceutical composition is administered locally to the site of the tumour of the nervous system. For instance in case of a skin tumour the pharmaceutical composition may be administered subcutaneously in close proximity of the tumorous tissue. It may also be preferred that the local administration of the pharmaceutical composition to the skin is achieved by crèmes or lotions that comprise the polypeptides.

Moreover in a preferred embodiment the local administration of the polypeptides may be preferably mediated by an implant such as a collagen sponge. To this end it may be preferred to soak the sponge in a pharmaceutical composition comprising the polypeptides and implant the sponge close to the site of the tumour. By doing so the polypeptides advantageously diffuse locally and can therefore site specific impede and/or reverse the growth of the tumour.

In further preferred embodiment the polypeptides may be locally administered by means of a hydrogel. Hydrogels are three-dimensional, cross-linked networks of water-soluble polymers. The person skilled in the art knows how to produce suitable hydrogels for the delivery of proteins or polypeptides (Hoare et al. 2008, Peppas et al. 2000, Hoffmann A. et al. 2012). In particular the density of the cross-linked network of the hydrogel may be advantageously optimized to achieve a porosity suited to load the polypeptides into the hydrogel. Subsequently the release of the polypeptides is governed by the diffusion of the peptides throughout the gel network. Therefore the release rate and thus the therapeutically effective amount of the polypeptides can be precisely tuned by optimizing the cross-linking density of the hydrogel. Moreover preferred hydrogels may also encompass an outer membrane optimized for the release of the polypeptides. The preferred hydrogels are biocompatible and are preferably implanted for a long term local supply of the polypeptides. In preferred embodiments the hydrogels may be implanted subcutaneously at or close to the site of the tumour. Transdermal administration of the polypeptides by use of hydrogels may also be envisioned. By means hydrogels a therapeutically effective dose of polypeptides can be advantageously localized to the site of the tumour, while minimizing the systemic dosage. Thereby a long term administration can be achieved with a sustained and site specific release and minimized side effects.

As used herein, "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or non-integrated, or relate to stably transfected nucleic acids.

As used herein, "polypeptide" shall mean both peptides and proteins. In this invention, the polypeptides may be naturally occurring or recombinant (i.e., produced via recombinant DNA technology), and may contain mutations (e.g., point, insertion and deletion mutations) as well as other covalent modifications (e.g., glycosylation and labelling (via biotin, streptavidin, fluorescein, and radioisotopes)) or other molecular bonds to additional components. For example, PEGylate proteins are encompassed by the scope of the present invention. PEGylation has been widely used as a post-production modification methodology for improving biomedical efficacy and physicochemical properties of therapeutic proteins. Applicability and safety of this technology have been proven by use of various PEGylated pharmaceuticals for many years (refer Jevsevar et al, Biotechnol J. 2010 January; 5(1):113-28). In some embodiments the polypeptides described herein are modified to exhibit longer in vivo half-lives and resist degradation when compared to unmodified polypeptides. Such modifications are known to a skilled person, such as cyclized polypeptides, polypeptides fused to Vitamin B12, stapled peptides, protein lipidization and the substitution of natural L-amino acids with D-amino acids (refer Bruno et al, Ther Deliv. 2013 November; 4(11): 1443-1467).

As used herein the term "a 0 to 10 amino acid addition or deletion at the N and/or C terminus of a sequence" means that the polypeptide may have a) 0, 1, 2, 3, 4, 5, 6, 7, 8, 9 or 10 additional amino acids at its N terminus and 0, 1, 2, 3, 4, 5, 6, 7, 8, 9 or 10 amino acids deleted at its C terminus or b) 0, 1, 2, 3, 4, 5, 6, 7, 8, 9 or 10 additional amino acids at its C terminus and 0, 1, 2, 3, 4, 5, 6, 7, 8, 9 or 10 nucleotides deleted at its N terminus, c) 0, 1, 2, 3, 4, 5, 6, 7, 8, 9 or 10 additional amino acids at its N terminus and 0, 1, 2, 3, 4, 5, 6, 7, 8, 9 or 10 additional amino acids at its N terminus or d) 0, 1, 2, 3, 4, 5, 6, 7, 8, 9 or 10 amino acids deleted at its N terminus and 0, 1, 2, 3, 4, 5, 6, 7, 8, 9 or 10 amino acids deleted at its C terminus.

Furthermore, in addition to the polypeptides described herein, peptidomimetics are also contemplated. Peptide analogs are commonly used in the pharmaceutical industry as non-peptide drugs with properties analogous to those of the template peptide. These types of non-peptide compound are termed "peptide mimetics" or "peptidomimetics" (Fauchere (1986) Adv. Drug Res. 15: 29; Veber and Freidinger (1985) TINS p. 392; and Evans et al. (1987) J. Med. Chem. 30: 1229) and are usually developed with the aid of computerized molecular modelling. Peptide mimetics that are structurally similar to therapeutically useful peptides may be used to produce an equivalent therapeutic or prophylactic effect. It may be preferred in some embodiments to use peptide mimetics in order to prolong the stability of the polypeptides, when administered to a subject. To this end peptide mimetics for the polypeptides may be preferred that are not cleaved by human proteasomes.

The polypeptides, nucleic acid molecules, gene therapy vectors or cells described herein may comprise different types of carriers depending on whether they are to be administered in solid, liquid or aerosol form, and whether they need to be sterile for such routes of administration as injection.

The active agent present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, directly, via a catheter, via a lavage, in cremes, in lipid compositions (e.g., liposomes), locally applied by sponges or by other method or any combination of the forgoing as would be known to one of ordinary skill in the art (see, for example, Remington's Pharmaceutical Sciences, 18th Ed. Mack Printing Company, 1990, incorporated herein by reference).

The present invention encompasses treatment of a patient by introducing a therapeutically effective number polypeptides, nucleic acids, gene therapy vectors or cells into a subject's bloodstream. As used herein, "introducing" polypeptides, nucleic acids, gene therapy vectors or cells into the subject's bloodstream shall include, without limitation, introducing such polypeptides, nucleic acids, gene therapy vectors or cells into one of the subject's veins or arteries via injection. Such administering can also be performed, for example, once, a plurality of times, and/or over one or more extended periods. A single injection is preferred, but repeated injections over time (e.g., quarterly, half-yearly or yearly) may be necessary in some instances. Such administering is also preferably performed using an admixture of polypeptides, nucleic acids, gene therapy vectors or cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline.

Administration may also occur locally, for example by injection into an area of the subject's body in proximity to a tumour disease. As used herein, in "proximity with" a tissue includes, for example, within 50 mm, 20 mm, 10 mm, 5 mm, within 1 mm of the tissue, within 0.5 mm of the tissue and within 0.25 mm of the tissue.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Additionally, such pharmaceutically acceptable carriers can be aqueous or non-aqueous solutions, suspensions, and emulsions, most preferably aqueous solutions. Aqueous carriers include water, alcoholic/aqueous solutions, emulsions and suspensions, including saline and buffered media. Parenteral vehicles include sodium chloride solution, Ringers dextrose, dextrose and sodium chloride, lactated Ringers and fixed oils. Intravenous vehicles include fluid and nutrient replenishers, electrolyte replenishers such as Ringers dextrose, those based on Ringers dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

As used herein, a "therapeutically effective amount" for the pharmaceutical composition includes, without limitation, the following amounts and ranges of amounts:

For a composition comprising a polypeptide according to the invention or preferred embodiment thereof: (i) from about $1\times10^{-3}$ to about $1\times10^{6}$ μg/kg body weight; (ii) from about $1\times10^{-2}$ to about $1\times10^{5}$ μg/kg body weight; (iii) from about $1\times10^{-1}$ to about $1\times10^{4}$ μg/kg body weight; (iv) from about $1\times10^{-1}$ to about $1\times10^{3}$ μg/kg body weight; (v) from about $1\times10^{-1}$ to about $1\times10^{2}$ μg/kg body weight; (vi) from about $1\times10^{-1}$ to about $0.5\times10^{2}$ μg/kg body weight; (vii) about $1\times10^{-2}$ μg/kg body weight; (viii) about $1\times10^{1}$ μg/kg body weight; (ix) about 10 μg/kg body weight (x) about $1\times10^{2}$ μg/kg body weight; (xi) about $5\times10^{3}$ μg/kg body weight.

For a composition comprising cells according to the invention or preferred embodiment thereof: (i) from about $1\times10^{2}$ to about $1\times10^{8}$ cells/kg body weight; (ii) from about $1\times10^{3}$ to about $1\times10^{7}$ cells/kg body weight; (iii) from about $1\times10^{4}$ to about $1\times10^{6}$ cells/kg body weight; (iv) from about $1\times10^{4}$ to about $1\times10^{5}$ cells/kg body weight; (v) from about $1\times10^{5}$ to about $1\times10^{6}$ cells/kg body weight; (vi) from about $5\times10^{4}$ to about $0.5\times10^{5}$ cells/kg body weight; (vii) about $1\times10^{3}$ cells/kg body weight; (viii) about $1\times10^{4}$ cells/kg body weight; (ix) about $5\times10^{4}$ cells/kg body weight; (x) about $1\times10^5$ cells/kg body weight; (xi) about $5\times10^5$ cells/kg body weight; (xii) about $1\times10^6$ cells/kg body weight; and (xiii) about $1\times10^7$ cells/kg body weight.

Human body weights envisioned include, without limitation, about 5 kg, 10 kg, 15 kg, 30 kg, 50 kg, about 60 kg; about 70 kg; about 80 kg, about 90 kg; about 100 kg, about 120 kg and about 150 kg.

Dosages of the viral gene therapy vector will depend primarily on factors such as the condition being treated, the selected gene, the age, weight and health of the patient, and may thus vary among patients. For example, a therapeutically effective human dosage of the viral vectors may be preferably in the range of from about 1 to about 1000 ml, preferably 10 to 100 ml, preferably 20 to 50 ml of saline solution containing concentrations of from about $1\times10^5$ to $1\times10^{12}$ preferably $1\times10^6$ to $1\times10^{11}$ more preferably $1\times10^7$ to $1\times10^{10}$ plaque forming units (pfu)/ml viruses. The dosage will be adjusted to balance the therapeutic benefit against any side effects. The levels of expression of the selected gene can be monitored to determine the selection, adjustment or frequency of dosage administration.

As used herein "inducible expression" or "conditional expression" relates to a state, multiple states or system of an expression of the polypeptide, wherein the polypeptide is preferably not expressed, or in some embodiments expressed at negligible or relatively low levels, unless there is the presence of one or more molecules (an inducer) or other set of conditions in the cell that allows for polypeptide expression. Inducible promoters may relate to either naturally occurring promoters that are expressed at a relatively higher level under particular biological conditions, or to other synthetic promoters comprising any given inducible element. Inducible promoters may refer to those induced by particular tissue- or micro-environments or combinations of biological signals present in particular tissue- or micro-environments, or to promoters induced by external factors, for example by administration of a small drug molecule or other externally applied signal.

As used herein the term "bio pump" or "drug factory" preferably describe the function of cells as a continuously producing source of the polypeptide, preferably at a therapeutically effective dosage. By administering cells to a subject particularly stable levels of the polypeptides according to the invention or preferred embodiments thereof can be provided. In the sense the bio pump, that is the cells, allow for a continuous supply that maintain levels of the polypeptides at a particular high and stable state, for example it may compensate for losses of the polypeptides for instance due to a degeneration of the polypeptides through proteasomes.

The terms "hydrogel", "gel" and the like, are preferably used interchangeably herein to refer to a material which is not a readily flowable liquid and not a solid. The term hydrogel is preferably meant to be a water insoluble, water-containing material. Examples of hydrogels include synthetic polymers such as polyhydroxyethyl methacrylate, poly(ethylene glycol) and chemically or physically cross-linked polyvinyl alcohol, polyacrylamide, poly(N-vinyl pyrolidone), polyethylene oxide, and hydrolysed polyacrylonitrile. Examples of hydrogels which are organic polymers include DNA hydrogels or covalent or ionically crosslinked polysaccharide-based hydrogels such as the polyvalent metal salts of alginate, pectin, carboxymethyl cellulose, heparin, hyaluronate and hydrogels from chitin, chitosan, pullulan, gellan and xanthan.

As used herein the term "tumour of the nervous system" refers to an abnormal growth and/or alternation of tissues or cells of the nervous system and refers thus to benign tumours or neoplasm as well as malignant tumours or neoplasm (cancers) of the nervous system in particular the central nervous system. Thus a tumour of the nervous system include in particular primary tumours of glial, neuronal, Schwann cell, pinealcyte, menningioma and melanoma, as well as sarcoma, lymphoma and multiple systemic malignancies that metastasize in the brain.

Specific examples of tumours of the nervous system include, but are not limited to, astrocytoma, glioblastoma, oligodendroglioma, ependymoma, choroid plexus carcinoma, angiocentric glioma, ganglioglioma, neurocytoma, dysplastic neuroepithelial tumour, paranglioma of the spinal cord, pineocytoma, pineocytoma, primitive neuroectodermal tumour, ganglioneuroma, schwannoma, neurofibroma, perinerioma, malignant peripheral nerve sheath tumour, meningioma, or haemangioblastoma.

A therapeutically effective amount of composition for the treatment of medical conditions associated with the treatment and/or prevention of medical conditions associated neurofibromatosis (NF), thus a genetic deficiency in neurofibromatosis type 1, neurofibromatosis type 2 and/or neurofibromatosis type 3 the therapeutically effective amount of the composition is preferably sufficient to achieve at least one, two, three, four or more of the following effects: (i) the reduction or amelioration of the severity of one or more NF symptoms; (ii) the reduction in the duration of one or more symptoms associated with NF; (iii) the prevention in the recurrence of a tumour or a symptom associated with NF; (iv) the regression of tumours and/or one or more symptoms associated therewith; (v) the reduction in hospitalization of a subject; (vi) the reduction in hospitalization length; (vii) the increase in the survival of a subject; (viii) the inhibition of the progression of tumours and/or one or more symptoms associated therewith; (ix) the enhancement or improvement of the therapeutic effect of another therapy; (x) a reduction or elimination of hearing loss, tinnitus, visual impairment, imbalance, or painful skin lesions associated with NF; (xi) a reduction in the growth of a tumour or neoplasm associated with NF; (xii) a decrease in tumour size (e.g., volume or diameter) of neurofibromas, plexiform neurofibromas, and/or NF2-associated tumours (e.g., meningiomas, schwannomas, ependymomas, etc.); (xiii) a reduction in the formation of a newly formed tumour, for example an NF-associated tumour such as neurofibromas, plexiform neurofibromas, or NF2-associated tumours (e.g., meningiomas, schwannomas, ependymomas, etc.); (xiv) eradication, removal, or control of primary, regional and/or metastatic tumours associated with NF; (xv) ease in removal of tumours by reducing vascularization prior to surgery; (xvi) a decrease in the number or size of metastases; (xvii) a reduction in mortality; (xviii) an increase in the tumour-free survival rate of patients; (xix) an increase in relapse free survival; (xx) an increase in the number of patients in remission; (xxi) a decrease in hospitalization rate; (xxii) the size of the tumour is maintained and does not increase or increases by less than the increase of a tumour after administration of a standard therapy as measured by conventional methods available to one of skill in the art, such as magnetic resonance imaging (MRI), dynamic contrast-enhanced MRI (DCE-MRI), X-ray, and computed tomography (CT) scan, or a positron emission tomography (PET) scan; (xxiii) the prevention of the development or onset of one or more symptoms associated with NF; (xxiv) an increase in the length of remission in patients; (xxv) the reduction in the number of symptoms associated with NF; (xxvi) an increase in symptom-free survival of NF patients; (xxvii) improvement in neural function, e.g., hearing, balance, tinnitus, or vision; (xxvi)

inhibition or decrease in tumour metabolism or perfusion; (xxvii) inhibition or decrease in angiogenesis or vascularization of the tumour; (xxviii) improvement in quality of life as assessed by methods well known in the art, e.g., tinnitus questionnaires; and/or (xxix) an improvement in hearing, hearing function, or word recognition.

As used herein, "treating" a subject afflicted with a disorder shall mean slowing, stopping or reversing the disorders progression. In the preferred embodiment, treating a subject afflicted with a disorder means reversing the disorders progression, ideally to the point of eliminating the disorder itself. As used herein, ameliorating a disorder and treating a disorder are equivalent. The treatment of the present invention may also, or alternatively, relate to a prophylactic administration of the active agents described herein. Such a prophylactic administration may relate to the prevention of any given medical disorder, or the prevention of development of said disorder, whereby prevention or prophylaxis is not to be construed narrowly under all conditions as absolute prevention. Prevention or prophylaxis may also relate to a reduction of the risk of a subject developing any given medical condition, preferably in a subject at risk of said condition.

FIGURES

The following figures are presented in order to describe particular embodiments of the invention, by demonstrating a practical implementation of the invention, without being limiting to the scope of the invention or the concepts described herein.

Short Description of the Figures:

FIG. 1: Schematic representation of an experimental protocol to assess the efficacy of rhNRG1 treatment and experimental results for serum levels of rhNRG1 and body weight of treated animals.

Figure 2:
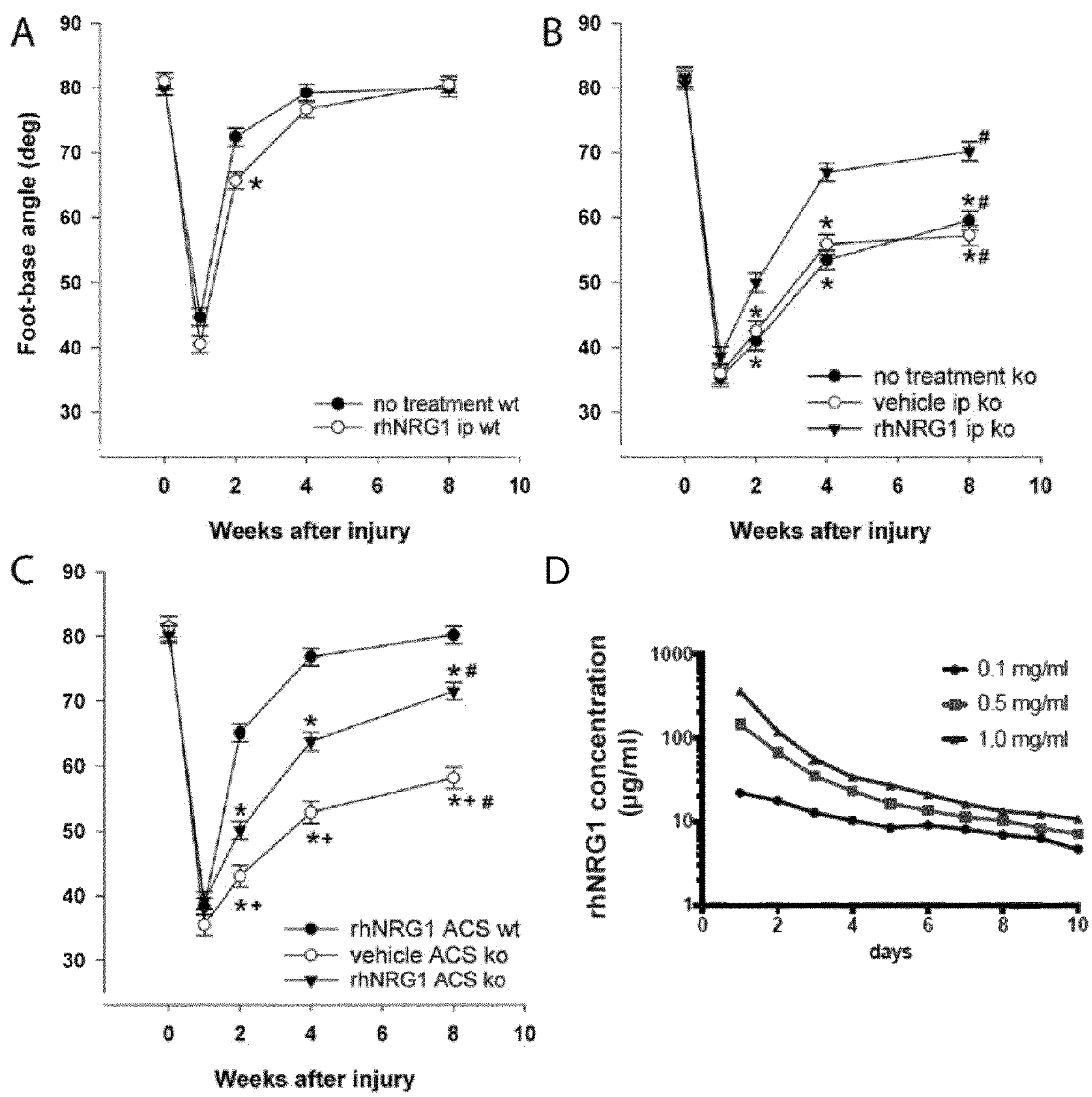

FIG. 2: Experimental results for functional nerve regeneration after nerve crush by treatment of rhNRG1.

Figure 3:
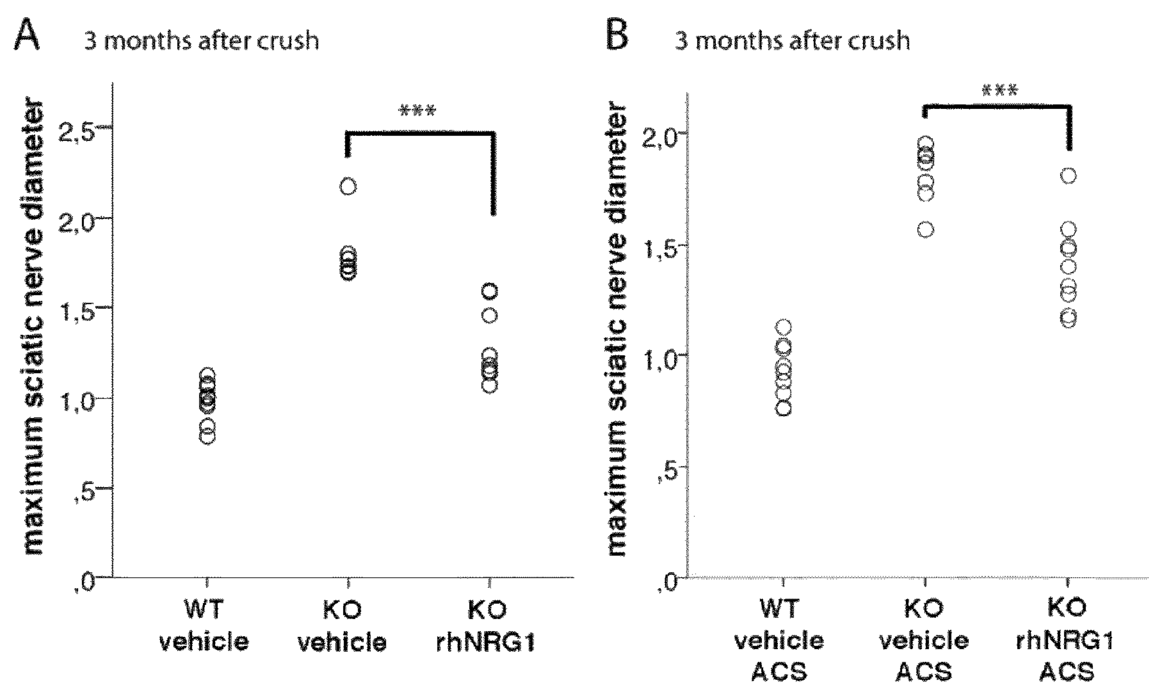

FIG. 3: Experimental results for sciatic nerve diameter following rhNRG1 treatment FIG. 4: Experimental results for signalling proteins with sciatic nerve lysates FIG. 5: Schematic representation of an experimental protocol and results to assess the efficacy of rhNRG1 treatment on pre-existing schwannomas.

Figure 6:
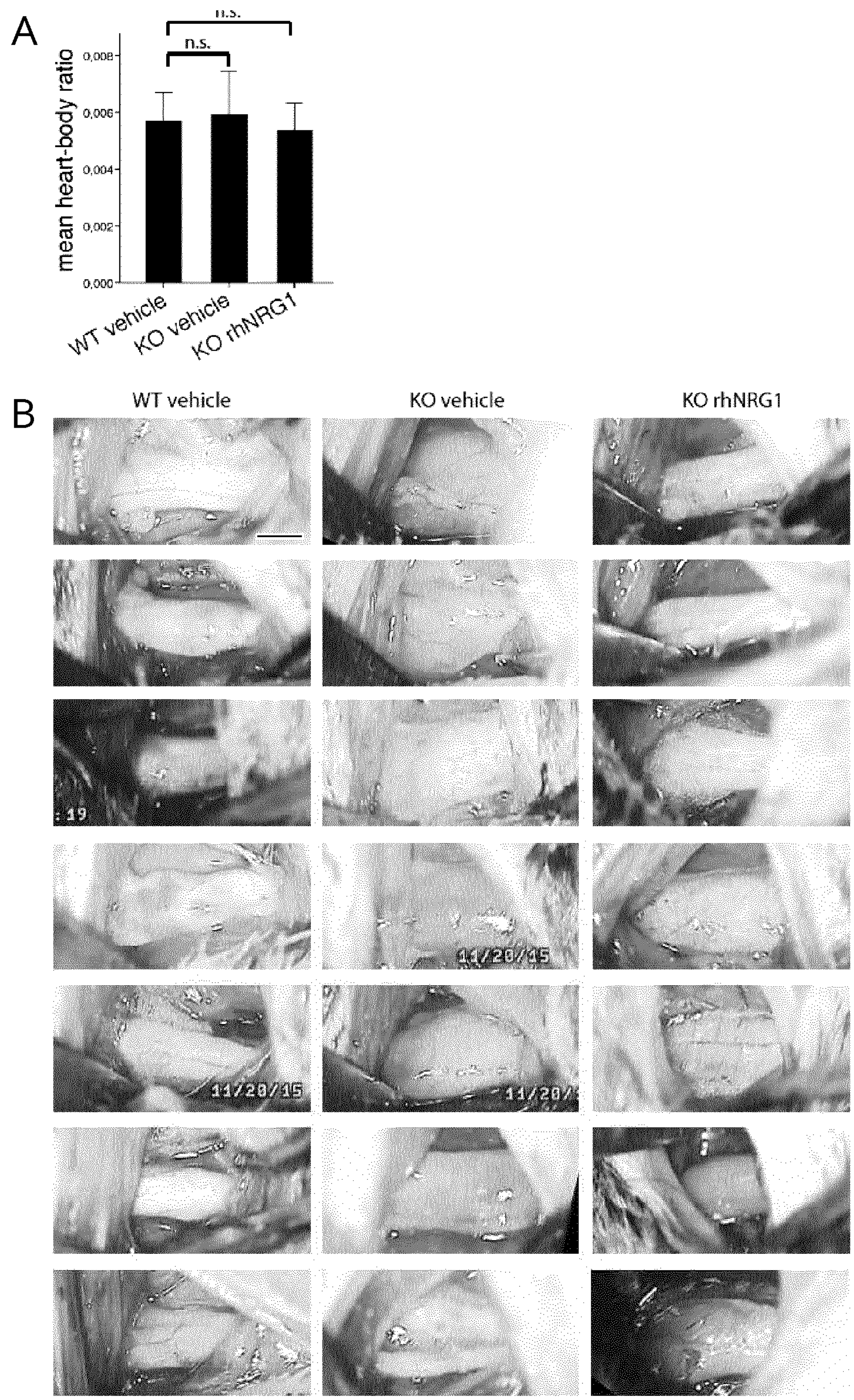

FIG. 6: Experimental results for the heart-body ratio of treated animals and visualization of the sciatic nerves.

Figure 7:
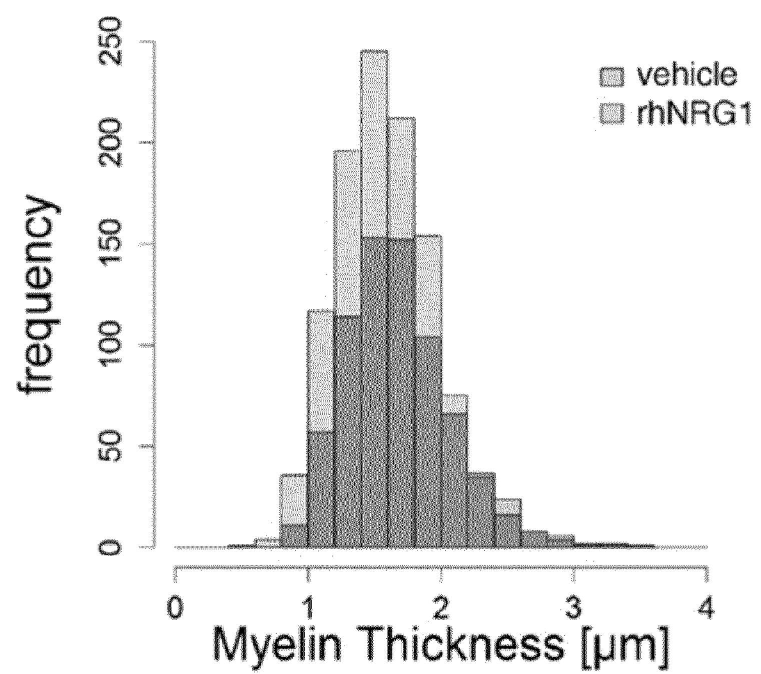

FIG. 7: Experimental results for the determination of myelin thickness in rhNRG1 treated and control animals FIG. 8 Experimental results for tumorlet burden in Nf2flox;Postn-Cre mutant mice after rhNRG1 treatment FIG. 9 Experimental results for tumor burden in Nf1flox; Postn-Cre mutant mice after rhNRG1 treatment

DETAILED DESCRIPTION OF THE FIGURES

FIG. 1: Study Design and rhNRG1 Pharmacokinetics

A, Schematic representation of the protocol used to assess the efficacy of rhNRG1 treatment on schwannoma growth after experimental sciatic nerve crush injury. B, Serum levels of rhNRG1 after single intraperitoneal injections of 10 μg rhNRG1 per kg body weight measured in pooled blood (n=4 animals; median). C, Body weight of animals receiving (genotype and treatment as indicated) was determined over 13 weeks.

FIG. 2: Functional Nerve Regeneration After Nerve Crush

A-C, Foot-base angle (FBA) quantification of Nf2flox; P0-Cre;Nefh-Cre mutant mice receiving no treatment (no treatment ko), saline injections (vehicle ip ko) or intraperitoneal administration of Neregulin1 (rhNRG1 ip ko). FBA baseline levels were measured before nerve injury (week 0). Functional motor recovery after sciatic nerve crush was assessed for 8 consecutive weeks (* $P<0.05$ for differences from non-treated animals; #$P<0.05$ for differences from baseline within same group; two-way ANOVA for repeated measures with Holm-Sidak post-hoc test; n=8 animals per genotype; mean±SEM). D, rhNRG1 release from rhNRG1-soaked sponges in vitro was estimated over time as protein concentration within PBS solution following 24 hours of incubation.

FIG. 3 Sciatic Nerve Diameter Following rhNRG1 Treatment

A and B, Quantification of sciatic nerve diameters 3 months after nerve crush injury. (A) Wildtype mice (WT vehicle) were compared with Nf2flox;P0-Cre;Nefh-Cre mutant mice receiving saline injections (KO vehicle) or intraperitoneal administration of Neregulin1 (KO rhNRG1; (* $P<0.001$ for differences between vehicle and rhNRG1-treated animals; n=8 animals per genotype; mean±SEM). (B) Wildtype mice (WT vehicle ACS) were compared with Nf2flox;P0-Cre;Nefh-Cre mutant mice receiving saline loaded absorbable collagen sponges (KO vehicle ACS) or rhNRG1 loaded sponges (KO rhNRG1 ACS; (* $P<0.001$ for differences between vehicle and rhNRG1-treated animals; n=8 animals per genotype; mean±SEM).

Figure 4:
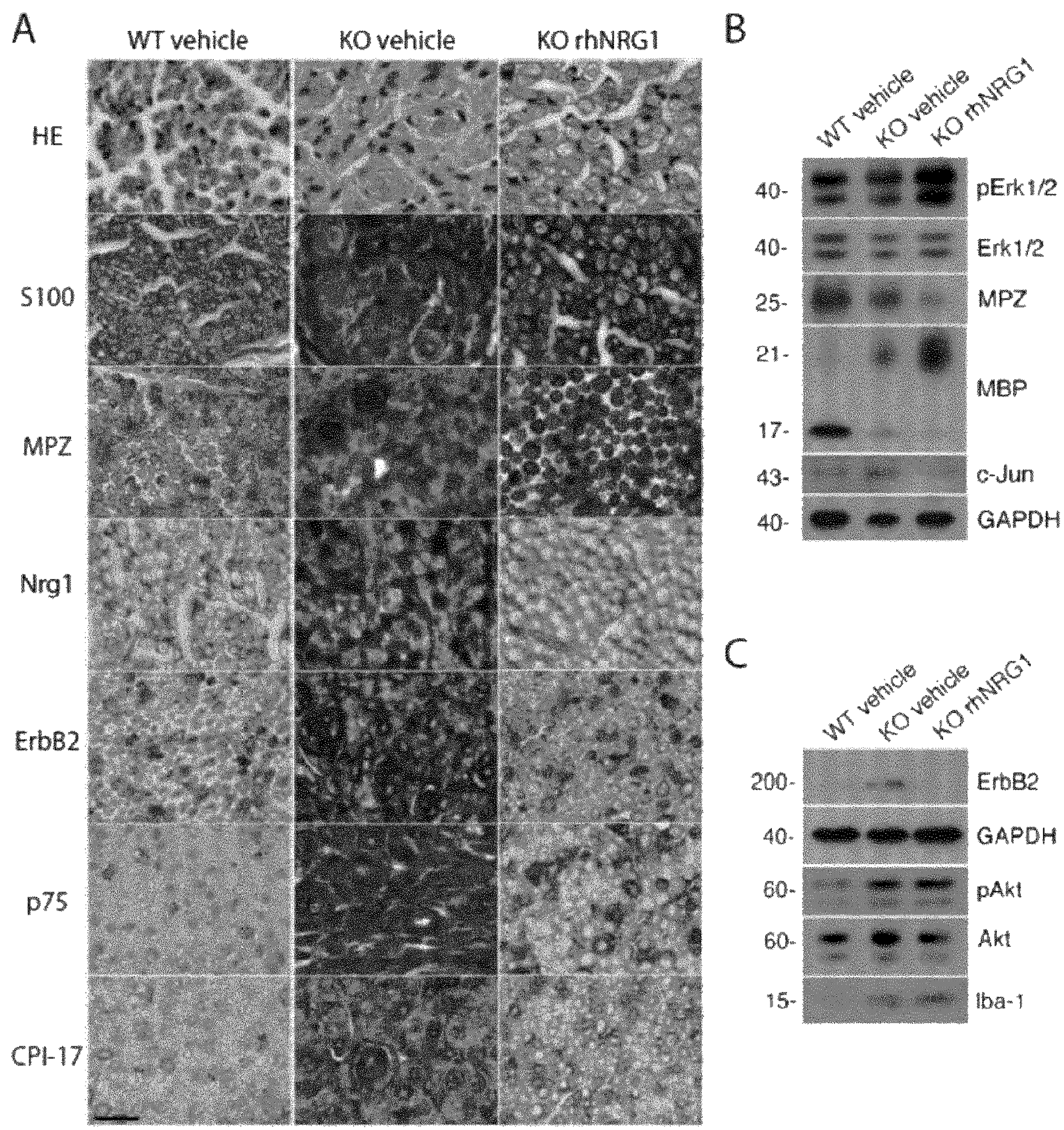

FIG. 4: Signalling and Neuropathological Assessment

A, Sciatic nerve cross sections of indicated cohorts 3 months after crush injury were either HE stained (a-f), or immunolabeled (brown color), for Schwann cell markers S100 and MPZ, Neuregulin1, the receptor tyrosine kinase ErbB2, p75 and CPI-17. Cell nuclei are visualized in blue. Scale bar represents 20 μm. B and C, Immunoblot of sciatic nerve lysates (pooled tissue from at least three different animals per indicated genotype was prepared from crushed sciatic nerves). (B) Immunoblot for Erk1/2, phospho-Erk1/2 (pErk1/2), myelin protein zero (MPZ), myelin basic protein (MBP), c-Jun and GAPDH as loading control (n=3). (C) Immunoblot for receptor tyrosine kinase ErbB2, Akt, phospho-Akt (pAkt), macrophage marker lba-1 and GAPDH as loading control (n=3).

Figure 5:
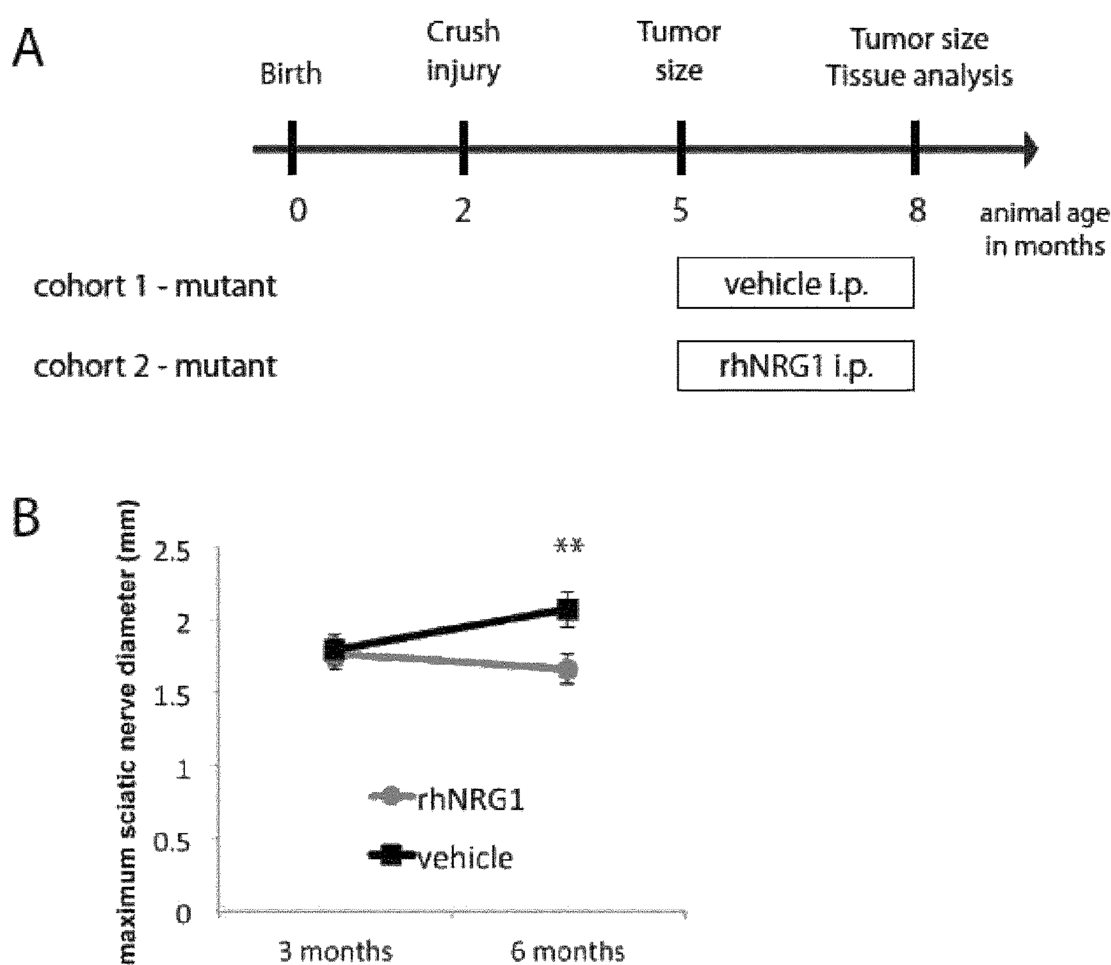

FIG. 5: Pre-Existing Tumors

A, Schematic representation of the protocol used to assess the efficacy of rhNRG1 treatment on pre-existing schwannomas. B, Quantification of maximum sciatic nerve diameters 3 and 6 months after nerve crush injury. Nf2flox;P0-Cre;Nefh-Cre mutant mice received either saline injections (vehicle) or intraperitoneal administration of rhNRH1 (** $P<0.01$ for differences between vehicle and rhNRG1-treated animals; n=6 animals per genotype; mean±SEM).

FIG. 6: Heart-Body Ratio and Sciatic Nerve Visualization

A, The heart-body ratio was determined in animals (genotype and treatment as indicated) after 13 weeks of treatment (n=8 animals per genotype; mean±SEM). B, Sciatic nerve visualization in situ 3 months after sciatic nerve crush. Representative images for assessment of sciatic nerve diameter as indicator for tumour size from wildtype mice (rhNRG1 ip wt) and Nf2flox;P0-Cre;Nefh-Cre mutant mice receiving saline injections (vehicle ip ko) or intraperitoneal administration of Neregulin1 (rhNRG1 ip ko).

FIG. 7: Myelin Thickness

Frequency blot of myelinated axons calculated from sciatic nerve cross sections of 5-month-old wildtype mice receiving either systemic rhNRG1 or vehicle treatment for 3 consecutive months.

Figure 8:
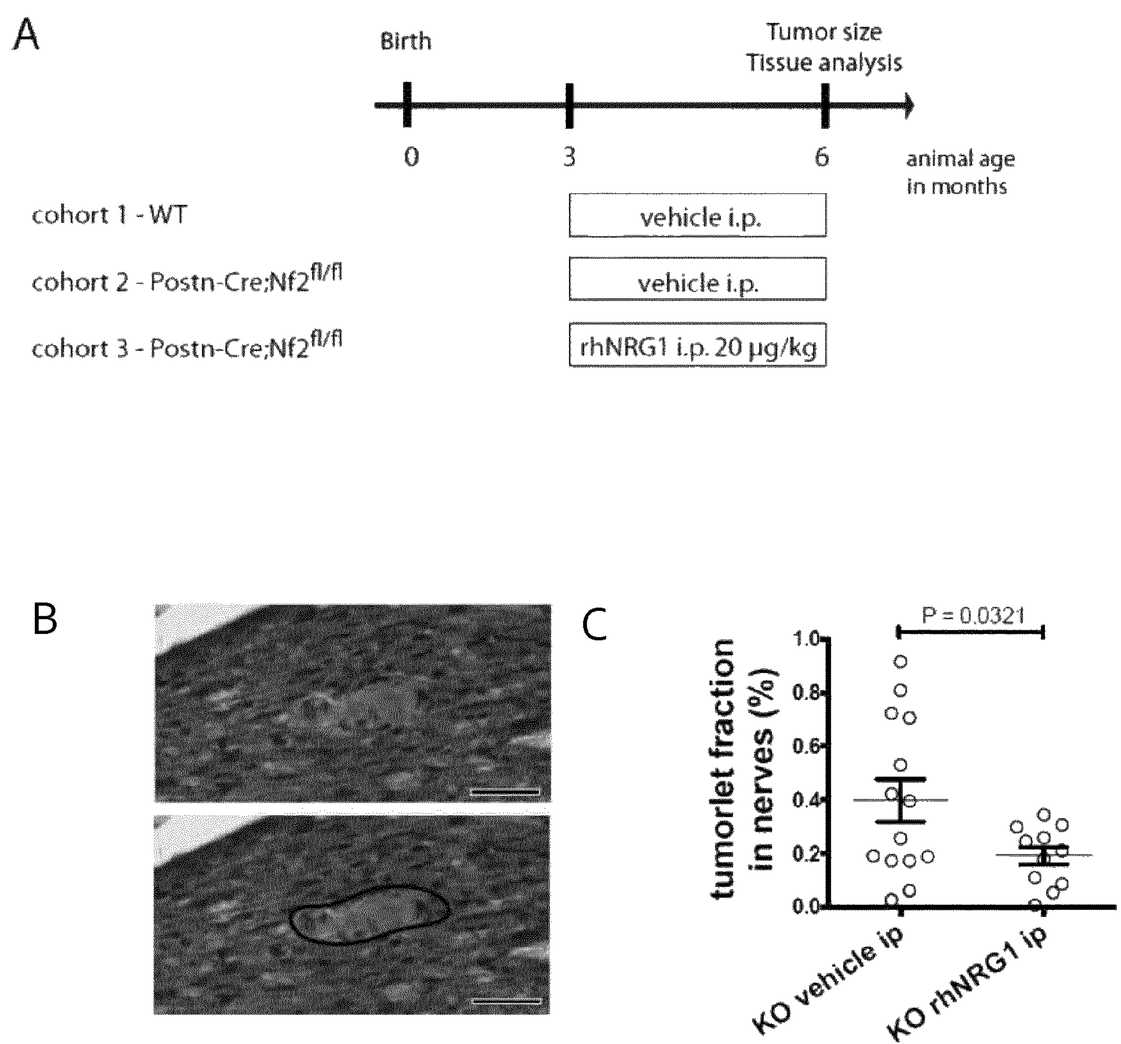

FIG. 8: Tumorlet Burden in Nerves of Nf2flox;Postn-Cre Mutant Mice

A, Study protocol used to assess the efficacy of systemic rhNRG1 treatment on tumorlet burden in Nf2flox;Postn-Cre animals. B, Representative longitudinal nerve section from six-month-old mutant Nf2flox;Postn-Cre mice indicating a circumscribed area of neoplastic Schwann cell proliferation (tumorlet). Scale bars represent 50 μm. C, Fraction of tumorlet tissue within total tissue was quantified as area covered by tumorlets in relation to the total nerve area in investigated nerve sections. Nf2flox;Postn-Cre mutant mice receiving intraperitoneal saline injections (KO vehicle ip) were compared to mutants on rhNRG1 injections (KO rhNRG1 ip; n=6 animals per genotype; mean±SEM).

Figure 9:
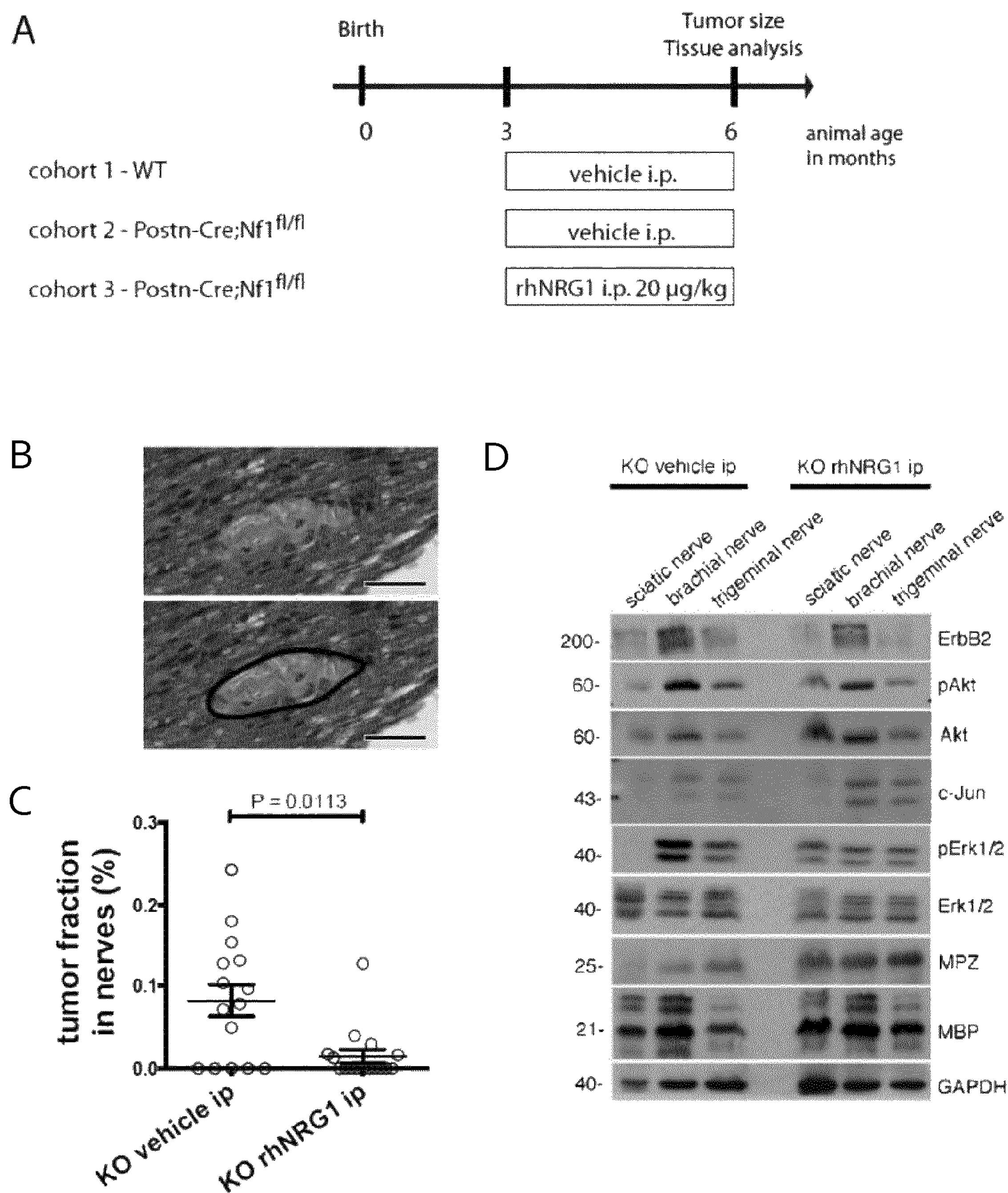

FIG. 9: Tumor Burden in Nerves of Nf1flox;Postn-Cre Mutant Mice

A, Study protocol used to assess the efficacy of systemic rhNRG1 treatment on schwannoma growth in Nf1flox; Postn-Cre animals. B, Representative longitudinal nerve section from six-month-old mutant Nf1flox;Postn-Cre mice indicating a circumscribed area of neurofibroma growth. Scale bars represent 50 μm. C, Fraction of tumor tissue within total tissue was quantified as area covered by tumor in relation to the total nerve area in investigated nerve sections. Nf1flox;Postn-Cre mutant mice receiving intraperitoneal saline injections (KO vehicle ip) were compared to mutants on rhNRG1 injections (KO rhNRG1 ip; n=6 animals per genotype; mean±SEM). D, Immunoblot of pooled tissue from at least three different animals prepared from sciatic nerves, brachial nerves, trigeminal nerves and dorsal root ganglions (DRG). Nf1flox;Postn-Cre mutant animals received either vehicle control injections (KO vehicle ip) or rhNRG1 treatment (KO rhNRG1 ip) over 3 months. Immunostaining for ErbB2, Akt, phospho-Akt (pAkt), c-Jun, Erk1/2, phospho-Erk1/2 (pErk1/2), myelin protein zero (MPZ), myelin basic protein (MBP) and GAPDH as loading control (n=3).

EXAMPLES

The examples show that the myelination promoting function of NRG1 as an instructive signal to de-differentiated Schwann cells has beneficial effects on schwannomas. In particular the examples show that by administering the EGF domain of recombinant human Neuregulin1 (rhNRG1) the development of schwannoma and neurofibroma can be efficiently prevented, reduced or reversed.

Materials and Methods Used in the Examples:

Experimental Animals

All animals had free access to food and water and were housed under constant temperature and humidity conditions on a 12/12-h light/dark cycle. Nf2flox animals (RIKEN BioResource Centre) were used to obtain combined conditional knockout of merlin in Schwann cells (P0-Cre line, The Jackson Laboratory, USA, stock 017928) and neurons (Nefh-Cre, The Jackson Laboratory, USA, stock 009102). Heterozygous knockout animals (P0-Cre;Nefh-Cre;$Nf2^{fl/+}$) were compared to wildtype littermates. Cre recombinase-specific genotyping was performed using the following primers: 5'-CCA CCA CCT CTC CAT TGC AC-3' (forward) and 5'-ATG TTT AGC TGG CCC AAA TG-3' (reverse) for P0-Cre (Feltri et al., 1999) as well as 5'-GGG CCA CCG CGG ATA TAA AA-3' (forward) and 5'-TGC GAA CCT CAT CAC TCG TT-3' (reverse) for Nefh-Cre recombinase (Hirasawa et al., 2001). Nf2flox;P0-Cre;Nefh-Cre animals were on a mixed C57BL/6-FVB/N background.

Nf2flox;Postn-Cre mice were obtained by crossing Nf2flox animals with Postn-Cre transgene mice. The Postn-Cre transgene was detected by PCR analysis with the following primers: P1 (CAT-TTG-GGC-CAG-CTA-AAC-AT) and P2 (CCC-GGC-AAA-ACA-GGT-AGT-TA). Nf2flox;Postn-Cre mice were on mixed FVB/NTac (Gehlhausen et al., 2015).

P0-Cre;Nefh-Cre;$Nf2^{fl/+}$, Nf2flox;Postn-Cre or Nf1flox; Postn-Cre mutant mice are herein also briefly referred to as 'mutant' mice or knockout (KO) mice Sciatic Nerve Crush Injury Unilateral injuries of sciatic nerves were accomplished according to a previously described method (Bauder and Ferguson, 2012). In brief, 8 to 10 week old mice were anesthetized using 2% isoflurane in 100% oxygen. Fur was then removed from one hind limb. After an appropriate incision of the skin, the gluteal musculature was separated in order to reveal the right sciatic nerve. Using haemostatic forceps (Ultra Fine Haemostat; #13021-12; tip width 0.6 mm; Fine Science Tools; Germany), the nerve was crushed once by the application of a defined pressure for 20 s. The locking mechanism of the haemostatic forceps with a series of interlocking teeth ensured reproducibility and standardization of crush injury. Finally, both the gluteal musculature and skin incision were sutured using appropriate surgical suture material.

rhNRG1 and Control Treatment

An EGF domain containing 7 kDa protein of recombinant human Neuregulin 1 ("rhNRG1") was purchased from Reprokine (#RKQ02297; USA). Protein was firstly resolved in $ddH_2O$ and further diluted in phosphate-buffered saline (PBS) to reach target concentrations. For systemic administration, 10 μg rhNRG1 per kg body weight was intraperitoneally injected into mice every other day. For local administration, Spongostan collagen sponges (#2484887; Ethicon; Germany) were cut into cubes of 2 mm edge length and incubated with 0.2 mg/ml rhNRG1 solution for one hour at room temperature prior to implantation. PBS solution without rhNRG1 served as vehicle control.

Absorbable Collagen Sponge (ACS) Performance in vitro.

Spongostan collagen sponges (#2484887; Ethicon; Germany) were cut into cubes of 2 mm edge length and incubated with a solution containing 0.1, 0.5 or 1.0 mg/ml rhNRG1 for 1 hour. rhNRG1-soaked sponges were transferred to a new dish of a 24-well plate filled with 0.5 ml PBS solution every day. rhNRG1 concentration of each dish was assess using standard BCA protein assay. Sponges that were initially incubated with PBS only served as control.

Blood Sampling and Serum Separation

To measure peripheral exposure of rhNRG1 in mice, up to 50 μl blood was sampled from mice for four consecutive days via bilateral retro-orbital plexus and facial veins. For serum preparation, collected blood was allowed to clot at room temperature for 1 hour before spinning for 20 minutes at 2,000 g.

Nrg1 ELISA Kit

Blood serum levels of rhNRG1 before and after intraperitoneal injection were measured using a commercially available kit according to manufacturer's instructions (#ab100614; Abcam; USA).

Single-Frame Motion Analysis (SFMA)

To evaluate locomotor function, mice were accustomed, in 3-4 trials, to beam-walking 1 week prior to surgery. In this test, the animal walks voluntarily from one end of a horizontal beam (length 1000 mm, width 40 mm) towards its home cage located at the other end of the beam. For all mice, a rear view of one walking trial was captured once prior to surgery and at different time-points after surgery with a Video camera and stored on a personal computer in Audio Video Interleaved (AVI) format. The video sequences were examined using VirtualDub 1.6.19 software. Selected frames, in which the animals were seen in defined phases of the step cycle, were used to measure the foot-base angle (FBA) as described in (Fey et al., 2010).

In situ Tumour Size Quantification

Three months after crush injury the right sciatic nerve of all animals was exposed surgically in order to assess sciatic nerve diameter as indicator for tumour size. Documentation was performed by video-assisted microscopy for each animal. Selected frames from the video files (using VirtualDub 1.6.19 software) were used to determine sciatic nerve diameter using ImageJ.

Neuropathological Assessment and Evaluation

For histological workup, paraformaldehyd fixed nerve samples were embedded in paraffin, cut at the site of the largest diameter and mounted as a tissue micro array. 4 μm thick cross sections were used for H&E staining and immunohistochemical labelling of S100 (1:8000; Dako), P0 (1:300; Bioss Antibodies), phospho-c-Jun (Ser73; 1:500; Cell Signalling; 8752), ErbB2 (1:500; Cell Signaling) and Arginase-1 (1:200; Santa Cruz; H-52) in an automated Ventana stainer (Ventana Medical Systems, USA) using standard antigen retrieval protocols (CC1st, no pretreatment for S100-protein). Onion-bulbs and schwannoma-like structures were assessed in H&E stained slides.

Immunohistochemistry and Cell Quantification

Immunohistochemistry was performed as described in (Schulz et al., 2010). Briefly, paraffin-embedded, longitudinal sections of sciatic nerves were rehydrated, boiled in 10 mM sodium citrate buffer (pH9) for 30 min in a microwave and subsequently treated with 0,5% Triton X-100 for 10 min. Sections incubated in 0.2% gelatine and 2% goat serum diluted in PBS at least 2 h. Sections submersed in the primary antibody solution overnight at 4° C. The following primary antibodies were used: Myelin protein zero (P0; 1:200; Abcam; ab39375), neurofilament (1:200; BioLegend; SMI312), myelin basic protein (MBP; 1:500; Millipore; MAB384)), Ki-67 (1:200; eBioscience; Clone: SolA15), lba-1 (1:200; Wako), and p75 (1:200; Merck Millipore; AB 1554). After vigorous washings, sections incubated with secondary antibody solution (Alexa488-, Alexa546- or Alexa647-conjugated anti-mouse, -rat, -chicken and -rabbit antibodies, 1:500 in PBS, Invitrogen) at room temperature for 2 h. Finally specimens washed in PBS, counterstained using DAPI (1 μg/ml PBS, 10 min) dehydrated and embedded. DAPI-stained cell nuclei or lba-1-positive cells were counted using ImageJ plugin 'Particle Analysis' from images acquired with 10× magnification after standardized background reduction and threshold setting.

Immunoblotting

Immunoblotting was performed as described in (Morrison et al., 2001). The following primary antibodies were used: phospho-c-Jun (Ser73; 1:1000; Cell Signalling; 8752), anti-Nrg1 (1:250; Santa Cruz; clone C-20), anti-Erk (1:500; Cell Signalling), anti-phospho-Erk (T202/Y204; 1:500; Cell Signalling), anti-ErbB2 (1:500; Cell Signalling), anti-GAPDH (1:1000; Santa Cruz; 6C5), anti-merlin (1:500; Santa Cruz; A19). Western blot results were quantified using Gel analysis software by ImageJ. Density values were normalized to actin and appropriate controls of transfection or wild-type tissue, respectively. In case of phospho-specific detection of proteins, their acquired densities were referred to signals derived from related pan-antibodies (e.g. phospho-Erk to Erk signals).

Morphometric Analysis of Nerve Sections

Analysis of axon calibre, myelination thickness and solidity factor was conducted on semi-thin and ultra-thin sections of the sciatic nerve removed from transcardially perfused mice. Mice were perfused with a solution containing 3% paraformaldehyde and 3% glutaraldehyde in 0.1 M phosphate buffer (pH 7.4). Sections were postfixed for 1 h and kept in fixative including 3% sucrose. Sections were obtained from the distal part of the sciatic nerve. Sectioning and staining were performed as described. Images of toluidine blue-stained semi-thin sections were taken using an Axioskop 2 MOT (Carl Zeiss, Germany) equipped with a 100× immersion oil objective and an Olympus XC50 digital camera (Olympus, Germany). Standardized settings for camera sensitivity, resolution (2,576×1,932 pixels) and brightness of illumination were used for all micrographs. Ultra-thin sections were analysed with an electron microscope (EM910, Carl Zeiss) equipped with an integrated TRS 1K digital camera (Carl Zeiss). Image analysis was conducted with ImageJ version 1.48u. RGB colour images obtained from semi-thin sections were split into single channels and the green channel was chosen for measurements. The image was contrasted using the auto function. Axon and myelin were circumscribed manually by the freehand selection tool. Based on the measured areas, the thicknesses of the axons and myelin sheaths were calculated. All calculations and statistics were done in R (http://www.r-project.org/).

Quantification of Tumorlets in Nf2flox;Postn-Cre Mice and Tumors in Nf1flox;Postn-Cre Mice.

PFA-fixed tissue blocks derived from rhNRG1 and control treated animals containing lower spinal cord, lumbar dorsal root ganglions (DRG) as well as distal nerve proportions were cut in 4 planes per animal. Photographs were subsequently scanned and analyzed using the NanoZoomer Digital Pathology Software. The total area occupied by peripheral nerve tissue and dorsal root ganglion (DRG) tissue in $mm^2$ was quantified separately. Likewise, neoplastic tissue regions were identified and quantified separately for peripheral nerves and DRG areas. All quantitative analyses of tumorlets in Nf2flox;Postn-Cre mice were performed in blinded manner.

Statistical Analysis

Comparisons between groups were made with unpaired t tests unless stated otherwise (SPSS software, Statistical Package for the Social Sciences, USA). For each experiment we calculated the p value (p), the t value (t) and the degree of freedom (df). Differences were considered significant when $p<0.05$. All values presented as means and their standard errors.

The following examples describe experimental results for rhNRG1 treatment of WT and mutant mice, which show that systemic and local administration of rhNRG1 effectively treats schwannoma and neurofibroma. Experimental procedures were performed as described in Example 1 (materials and methods) and corresponding experimental data is depicted in FIGS. 1-9.

Example 1 rhNRG1 Treatment Animals does not Lead to Body Weight Reduction, but Yields High Levels of Serum All mice underwent the defined study protocol as shown in FIG. 1A. Crush injury-induced schwannoma formation was provoked in 2-month-old mice. Subsequently, administration of rhNRG1 was performed both systemically (by intraperitoneal injection) and locally (by rhNRG1-containing absorbable collagen sponges (ACS)). Vehicle saline solution was given to control animals. In order to assess the bioavailability of intraperitoneally injected rhNRG1 (10 μg per kg body weight), rhNRG1 serum levels were evaluated. Strikingly, rhNRG1 levels reached a peak 2 days after injection (FIG. 1B). Because rhNRG1 treatment at high doses was reportedly accompanied by a decrease in body weight (Fledrich et al., 2014), we weekly checked the weight of systemically treated animals. A significant decline in body weight at the chosen dosage was, however, not observed (FIG. 1C).

Example 2 rhNRG1 Protein Treatment Improves Functional Recovery After Sciatic Nerve Crush

It was tested whether rhNRG1 protein replacement can improve functional recovery of mice over a time period of 8 weeks after sciatic nerve crush. Performing single-frame motion analysis (SFMA) showed that systemic rhNRG1 application to wildtype animals does not enhance regeneration (FIG. 2A). However, Nf2flox;P0-Cre;Nefh-Cre mutant mice receiving continuous intraperitoneal rhNRG1 injections every other day displayed significantly improved recovery compared to mice without treatment or saline control (FIG. 2B).

In addition to the systemic administration of rhNRG1, the efficacy of rhNRG1 on schwannoma growth was investigated when applied locally. To that end, biodegradable and biocompatible absorbable collagen sponges (ACS) were used to load either rhNRG1 protein or saline control solution. ACS have been successfully used for the locally-restricted delivery of proteins in preclinical settings (Friess, 1998) and have applications in the clinical setting for hemostasis (Browder and Litwin, 1986). Absorbable collagen sponges (ACS) cubes were incubated with solutions containing different concentrations of rhNRG1 (FIG. 2D). Subsequent analysis concerning the amount of rhNRG1 protein secreted by ACS over time in vitro showed a stable expulsion of rhNRG1 by the collagen sponges (FIG. 2D). In vivo biostability analysis further determined that ACS cubes in close proximity to sciatic nerves were still detectable two weeks after the implantation.

Consistently with the results for the systematic administration, the local administration of rhNRG1 using absorbable collagen sponges was able to increase functional regeneration in Nf2flox;P0-Cre;Nefh-Cre mutant mice compared to control treatment (FIG. 2C).

Example 3 rhNRG1 Protein Treatment Impedes the Development of Schwannoma

Sciatic nerve crush injury was conducted on WT mice and Nf2flox;P0-Cre;Nefh-Cre mutant mice as described above. Three months after crush injury wildtype animals showed anatomically regular sciatic nerves with a mean diameter of about 1 mm (WT vehicle, FIG. 3A). In contrast, the sciatic nerve of Nf2flox;P0-Cre;Nefh-Cre mutant mice receiving saline control injections appeared massively enlarged resulting in a 2-fold gain in nerve diameter to about 2 mm (KO vehicle, FIG. 3A). The systemic administration of rhNRG1, however, could significantly ameliorate this nerve swelling and resulted in a reduced nerve diameter of about 1.5 mm (KO rhNRG1, FIG. 3A). Slightly minor effects were seen in Nf2flox;P0-Cre;Nefh-Cre mutant mice receiving a local therapy of rhNRG1 using absorbable collagen sponges (rhNRG1 ACS) when compared to Nf2flox;P0-Cre;Nefh-Cre mutant mice receiving the control therapy (FIG. 3B). 3 months after crush injury wildtype animals showed anatomically regular sciatic nerves with a mean diameter of about 1 mm (WT vehicle ACS, FIG. 3B). The sciatic nerve of Nf2flox;P0-Cre;Nefh-Cre mutant mice receiving control Spongostan collagen sponges incubated with a PBS solution exhibited an enlarged nerve diameter of about 1.8 mm after three months (KO vehicle ACS, FIG. 3B). Local administration of rhNRG1 to Nf2flox;P0-Cre;Nefh-Cre mutant mice by treatment of Spongostan collagen sponges incubated with a 0.2 mg/ml rhNRG1 solution reduced the nerve swelling and resulted in a nerve diameter of about 1.4 mm after 3 month (KO rhNRG1 ACS, FIG. 3B). Moreover by determining the myelin thickness, structural integrity of non-crushed, intact nerves was assessed (FIG. 7). The long-term treatment with rhNRG1 over 8 weeks had no obvious impact on the microarchitecture of intact nerves as indicated by similar g-ratio values for rhNRG1 and PBS control treated animals.

Example 4 rhNRG1 Protein Treatment Leads to Differentiation of De-Differentiated Schwann Cells Sciatic nerve crush injury was performed on WT and Nf2flox;P0-Cre;Nefh-Cre mutant animals as described in Example 1. The Nf2flox;P0-Cre;Nefh-Cre mutant animals were intraperitoneally injected every day with 10 μg of rhNRG1 per kg body weight (KO rhNRG1). For a control a PBS solution was systemically administered to WT animals and Nf2flox;P0-Cre;Nefh-Cre mutant animals (WT vehicle and KO vehicle). Sciatic nerve lysates were taken from animals after 3 month of treatment upon which immunochemistry was performed as described in Example 1.

Neuropathological assessment of nerve tissue 3 months after crush injury revealed regular normal nerve composition in wildtype animals treated with saline control injections (FIG. 2A, left panel), accompanied by normal expression of the Schwann cell differentiation markers S100 and myelin protein zero (MPZ). Neuregulin1 and ErbB2 immunoreactivity was localized to axonal membrane and Schwann cells, respectively. The p75 neurotrophin receptor (marker for immature non-myelinating Schwann cells) showed expression restricted to scattered locations only. The putative schwannoma marker CPI-17, up-regulated in human schwannomas but no other PNS nerve tumors (Nagel et al., 2016), also showed only weak immunostaining in sciatic nerves wildtype animals receiving control injections.

In contrast, nerves of vehicle-treated KO (P0-Cre;Nefh-Cre;$Nf2^{fl/+}$) animals demonstrated large clusters of unordered Schwann cells with large concentric multilayered onion bulbs 3 months after nerve crush injury (FIG. 2A, middle panel). S100 and MPZ expression appeared to be increased in comparison to wildtype mice. Consistently, Neuregulin1 and ErbB2 immunoreactivity was markedly enhanced in these nerves. Up-regulated p75 and CPI-17 expression suggests the presence of more immature non-myelinating Schwann cells and the classification as schwannoma, respectively.

Sciatic nerves of rhNRG1-treated KO (P0-Cre;Nefh-Cre; $Nf2^{fl/+}$) animals, instead, showed almost regular regeneration 3 months after crush injury. S100 and MPZ immunoreactivity was restricted to Schwann cells with myelinating phenotype. Strikingly, the expression of both Neuregulin1 and the receptor tyrosine kinase ErbB2 was greatly reduced following systemic rhNRG1 treatment when compared with saline treated animals of the same genotype. Furthermore, the number of immature Schwann cells appeared relevantly decreased due to rhNRG1 injections as indicated p75 staining. The immunoreactivity of the presumptive schwannoma marker CPI-17 was also relevantly lower than in KO animals receiving control injections.

Sciatic nerve lysates taken from Nf2flox;P0-Cre;Nefh-Cre animals after 3 months of rhNRG1 treatment demonstrated reduced expression of the myelin protein zero (MPZ) as a marker for differentiated Schwann cells in both knockout animal groups (KO vehicle and KO rhNRG1, FIG. 4B). Furthermore, the 17 kDa-myelin basic protein (MBP) isoform (Boggs 2006) showed a remarkable reduced expression in both knockout groups compared to wildtype littermates (FIG. 4B). However, the 21.5-kDa MBP isoform, which has been repeatedly reported to be re-myelination-specific (Capello et al. 1997, He et al. 2012), showed a strong up-regulation in animals receiving treatment with rhNRG1 (KO rhNRG1). This result demonstrates an increased Schwann cell differentiation upon rhNRG1 treatment. Consistently, c-Jun levels as marker for undifferentiated Schwann cells was reduced in knockout animals receiving systemic rhNRG1 injections (FIG. 4B). ErbB2, one of the most abundantly expressed receptor tyrosine kinases in human schwannomas (Boin et al., 2014), shows high expression in vehicle treated knockout animals but normal expression in rhNRG1 treated mice (FIG. 4C). The macrophage number in the nerve tissue, as indicated by lba-1 immunoblot (FIG. 4C), was not influenced by systemic rhNRG1 treatment.

Example 5 rhNRG1 Protein Treatment Reduces Tumor Growth of Pre-Established Schwannoma

Two cohorts of animals underwent crush injury-induced schwannoma induction at the right sciatic nerve as described above (FIG. 5A). After a period of three months without any treatment, the maximum sciatic nerve diameter was found to be equal in both groups (FIG. 5B). Then knockout animals (Nf2flox;P0-Cre;Nefh-Cre mutant animals) received either systemic rhNRG1 treatment or vehicle control applications for three months (FIG. 5A). As a result of rhNRG1 treatment, tumor size was markedly smaller compared to vehicle administration. (FIG. 5B)

Example 6 rhNRG1 Protein Treatment On Schwannoma Growth in Nf2flox;Postn-Cre Mice

The in vivo results on the efficacy of rhNRG1 on schwannoma growth was tested as described in Example 1 however in a another animal model of schwannoma disease, the well-established Nf2flox;Postn-Cre mouse line, wherein a conditional Nf2 gene deletion is facilitated by the Periostin-Cre driver line (Nf2flox;Postn-Cre).

In this model all animals spontaneously develop spinal, peripheral and cranial nerve schwannomas over time (Gehlhausen et al., 2015). 4-month-old mutant Nf2flox;Postn-Cre animals as well as their corresponding wildtype littermates were either treated with saline control injections or intraperitoneal rhNRG1 administration for three months (FIG. 8A). As a rhNRG1 dosage of 10 μg/kg was well tolerated in Nf2flox;P0-Cre;Nefh-Cre animals, Nf2flox;Postn-Cre mice were treated with an increased dosage of 20 μg rhNRG1 per kg bodyweight. In order to test rhNRG1 efficacy, the phenotypic feature of Nf2flox;Postn-Cre mutant animals to develop neoplastic Schwann cell proliferation areas (tumorlets) was deployed. Tumorlets are considered schwannoma precursors in spinal and peripheral nerves (FIG. 8B). Quantification of the area occupied by tumorlets in relation to the total area of investigated nerve tissue revealed a significant reduction of tumorlet fraction in rhNRG1-treated animals as compared to control animals (FIG. 8C).

Example 7 rhNRG1 Protein Treatment Reduces Neurofibroma Growth in Nf1flox;Postn-Cre Mice Another closely related but not similar entity of Schwann cell tumors are neurofibromas. As opposed to schwannomas, Schwann cells represent the primary neoplastic cell component of neurofibromas (Stemmer-Rachamimov et al., 2004; Rodriguez et al., 2012), but also incorporate a mixture of non-neoplastic components, including axons, perineurial cells, fibroblasts and inflammatory cells. In order to test a possible effect of rhNRG1 treatment on these tumors, which are a typical manifestation of the hereditary disease Neurofibromatosis type 1 (NF1), 4-month-old mutant Nf1flox; Postn-Cre animals as well as wildtype littermates were either treated with saline control injections or intraperitoneal rhNRG1 administration for three months (FIG. 9A). Analysis and quantification of neurofibromas originating from distal parts of the nervous system revealed a significant effect of rhNRG1 treatment (FIGS. 9B and 9C). Biochemical analysis of nerve tissue from Nf1flox;Postn-Cre mice illustrate further a reduced ErbB2 expression following rhNRG1 treatment as well as enhanced Schwann cell differentiation indicated by increased myelin protein zero (MPZ) expression (FIG. 9D).

REFERENCES

Asthagiri A R, Parry D M, Butman J A, Kim H J, Tsilou E T, Zhuang Z, Lonser R R (2009) Neurofibromatosis type 2. Lancet 373:1974-1986.

Bakker A C, La Rosa S, Sherman L S, Knight P, Lee H, Pancza P, Nievo M (2016) Neurofibromatosis as a gateway to better treatment for a variety of malignancies. Progress in neurobiology.

Bauder A R, Ferguson T A (2012) Reproducible mouse sciatic nerve crush and subsequent assessment of regeneration by whole mount muscle analysis. Journal of visualized experiments: JoVE.

Boggs J M (2006) Myelin basic protein: a multifunctional protein. Cellular and molecular life sciences: CMLS 63:1945-1961.

Boin A, Couvelard A, Couderc C, Brito I, Filipescu D, Kalamarides M, Bedossa P, De Koning L, Danelsky C, Dubois T, Hupe P, Louvard D, Lallemand D (2014) Proteomic screening identifies a YAP-driven signaling network linked to tumor cell proliferation in human schwannomas. Neuro-oncology 16:1196-1209.

Browder I W, Litwin M S (1986) Use of absorbable collagen for hemostasis in general surgical patients. The American surgeon 52:492-494.

Capello E, Voskuhl R R, McFarland H F, Raine C S (1997) Multiple sclerosis: re-expression of a developmental gene in chronic lesions correlates with remyelination. Annals of neurology 41:797-805.

Evans D G, Howard E, Giblin C, Clancy T, Spencer H, Huson S M, Lalloo F (2010) Birth incidence and prevalence of tumor-prone syndromes: estimates from a UK family genetic register service. American journal of medical genetics Part A 152A:327-332.

Feltri M L, D'Antonio M, Previtali S, Fasolini M, Messing A, Wrabetz L (1999) P0-Cre transgenic mice for inactivation of adhesion molecules in Schwann cells. Annals of the New York Academy of Sciences 883:116-123.

Fey A, Schachner M, Irintchev A (2010) A novel motion analysis approach reveals late recovery in C57BL/6 mice and deficits in NCAM-deficient mice after sciatic nerve crush. Journal of neurotrauma 27:815-828.

Fleck D, van Bebber F, Colombo A, Galante C, Schwenk B M, Rabe L, Hampel H, Novak B, Kremmer E, Tahirovic S, Edbauer D, Lichtenthaler S F, Schmid B, Willem M, Haass C (2013) Dual cleavage of neuregulin 1 type III by BACE1 and ADAM17 liberates its EGF-like domain and allows paracrine signaling. The Journal of neuroscience: the official journal of the Society for Neuroscience 33:7856-7869.

Fledrich R, Stassart R M, Klink A, Rasch L M, Prukop T, Haag L, Czesnik D, Kungl T, Abdelaal T A, Keric N, Stadelmann C, Bruck W, Nave K A, Sereda M W (2014) Soluble neuregulin-1 modulates disease pathogenesis in rodent models of Charcot-Marie-Tooth disease 1A. Nature medicine 20:1055-1061.

Fricker F R, Lago N, Balarajah S, Tsantoulas C, Tanna S, Zhu N, Fageiry S K, Jenkins M, Garratt A N, Birchmeier C, Bennett D L (2011) Axonally derived neuregulin-1 is required for remyelination and regeneration after nerve injury in adulthood. The Journal of neuroscience: the official journal of the Society for Neuroscience 31:3225-3233.

Friess W (1998) Collagen-biomaterial for drug delivery. European journal of pharmaceutics and biopharmaceutics: official journal of Arbeitsgemeinschaft fur Pharmazeutische Verfahrenstechnik eV 45:113-136.

Gehlhausen J R, Park S J, Hickox A E, Shew M, Staser K, Rhodes S D, Menon K, Lajiness J D, Mwanthi M, Yang X, Yuan J, Territo P, Hutchins G, Nalepa G, Yang F C, Conway S J, Heinz M G, Stemmer-Rachamimov A, Yates C W, Wade Clapp D (2015) A murine model of neurofibromatosis type 2 that accurately phenocopies human schwannoma formation. Human molecular genetics 24:1-8.

Gorzelany J A, de Souza M P (2013) Protein replacement therapies for rare diseases: a breeze for regulatory approval? Science translational medicine 5:178fs110.

Hagel C, Dornblut C, Schulz A, Wiehl U, Friedrich R E, Huckhagel T, Mautner V F, Morrison H (2016) The putative oncogene CPI-17 is up-regulated in schwannoma. Neuropathology and applied neurobiology.

He X, Knepper M, Ding C, Li J, Castro S, Siddiqui M, Schachner M (2012) Promotion of spinal cord regeneration by neural stem cell-secreted trimerized cell adhesion molecule L1. PloS one 7:e46223.

Hirasawa M, Cho A, Sreenath T, Sauer B, Julien J P, Kulkarni A B (2001) Neuron-specific expression of Cre recombinase during the late phase of brain development. Neuroscience research 40:125-132.

Hoare T., Kohane D. (2008) Hydrogels in drug delivery: Progress and challenges. Polymer 49:1993-2007.

Hoffmann A. (2012) Hydrogels for biomedical applications. Advanced drug delivery reviews 64:18-23.

Jessen K R, Mirsky R (2005) The origin and development of glial cells in peripheral nerves. Nature reviews Neuroscience 6:671-682.

Kastin A J, Akerstrom V, Pan W (2004) Neuregulin-1-beta1 enters brain and spinal cord by receptor-mediated transport. Journal of neurochemistry 88:965-970.

Mautner V F, Nguyen R, Kutta H, Fuensterer C, Bokemeyer C, Nagel C, Friedrich R E, Panse J (2010) Bevacizumab induces regression of vestibular schwannomas in patients with neurofibromatosis type 2. Neuro-oncology 12:14-18.

Mei L, Xiong W C (2008) Neuregulin 1 in neural development, synaptic plasticity and schizophrenia. Nature reviews Neuroscience 9:437-452.

Mendes-Ferreira P, De Keulenaer G W, Leite-Moreira A F, Bras-Silva C (2013) Therapeutic potential of neuregulin-1 in cardiovascular disease. Drug discovery today 18:836-842.

Michailov G V, Sereda M W, Brinkmann B G, Fischer T M, Haug B, Birchmeier C, Role L, Lai C, Schwab M H, Nave K A (2004) Axonal neuregulin-1 regulates myelin sheath thickness. Science 304:700-703.

Morrison H, Sherman L S, Legg J, Banine F, Isacke C, Haipek C A, Gutmann D H, Ponta H, Herrlich P (2001) The NF2 tumor suppressor gene product, merlin, mediates contact inhibition of growth through interactions with CD44. Genes & development 15:968-980.

Newbern J, Birchmeier C (2010) Nrg1/ErbB signaling networks in Schwann cell development and myelination. Seminars in cell & developmental biology 21:922-928.

Neeltje A. Kootstra, Inder M. Verma (2009), Gene therapy with viral vectors, Annual Review of Pharmacology and Toxicology 43:413-439.

Peppas N., Bures, P. Leobandung W., Ichikawa H. (2000) Hydrogels in pharmaceutical formulation European Journal of Pharmaceutics and Biopharmaceutics, 50:27-46.

Plotkin S R, Stemmer-Rachamimov A O, Barker F G, 2nd, Halpin C, Padera T P, Tyrrell A, Sorensen A G, Jain R K, di Tomaso E (2009) Hearing improvement after bevacizumab in patients with neurofibromatosis type 2. The New England journal of medicine 361:358-367.

Prem Seth (2005) Vector-mediated cancer gene therapy: An overview, Cancer Biology & Therapy, 4:5, 512-517.

Rodriguez F J, Folpe A L, Giannini C, Perry A (2012) Pathology of peripheral nerve sheath tumors: diagnostic overview and update on selected diagnostic problems. Acta neuropathologica 123:295-319.

Schulz A, Zoch A, Morrison H (2014a) A neuronal function of the tumor suppressor protein merlin. Acta neuropathologica communications 2:82.

Schulz A, Geissler K J, Kumar S, Leichsenring G, Morrison H, Baader S L (2010) Merlin inhibits neurite outgrowth in the CNS. The Journal of neuroscience: the official journal of the Society for Neuroscience 30:10177-10186.

Schulz A, Kyselyova A, Baader S L, Jung M J, Zoch A, Mautner V F, Hagel C, Morrison H (2014b) Neuronal merlin influences ERBB2 receptor expression on Schwann cells through neuregulin 1 type III signalling. Brain: a journal of neurology 137:420-432.

Slusarz K M, Merker V L, Muzikansky A, Francis S A, Plotkin S R (2014) Long-term toxicity of bevacizumab therapy in neurofibromatosis 2 patients. Cancer chemotherapy and pharmacology 73:1197-1204.

Stemmer-Rachamimov A O et al. (2004) Comparative pathology of nerve sheath tumors in mouse models and humans. Cancer research 64:3718-3724.

Stove C et al. (2004) Roles for neuregulins in human cancer. Clinical & Experimental Metastasis 21: 665-684.

Walther W., Stein U. (2000), Viral Vectors for gene transfer, Drugs 60 (2): 249-271.

Waehler R., Stephen J. Russell & David T. Curiel Engineering targeted viral vectors for gene therapy, Nature Reviews Genetics 8, 573-587.

The invention claimed is:

1. A method for treating a tumor of the nervous system in a subject, the method comprising administering a polypeptide to the subject, wherein said polypeptide comprises an EGF-like domain of a neuregulin protein.

2. The method according to claim 1, wherein the polypeptide is a soluble fragment of a neuregulin protein.

3. The method according to claim 1, wherein the polypeptide comprises of an amino acid sequence according to one of SEQ ID NO 9-14 or an amino acid sequence with an identity of at least 80%, preferably of at least 90%, to any one of SEQ ID NO 9-14.

4. The method according to claim 1, wherein the polypeptide consists of an amino acid sequence according to SEQ ID NO 9 or of an amino acid sequence with an identity of at least 80% to SEQ ID NO 9.

5. The method according to claim 1, wherein the tumor is a tumor of the cranial or peripheral nerves.

6. The method according to claim 1, wherein the tumor is a malignant nerve sheath tumor.

7. The method according to claim 1, wherein the tumor is a schwannoma.

8. The method according to claim 1, wherein the tumor is a neurofibroma.

9. The method according to claim 1, for treating medical conditions associated with one or more of genetic deficiency in neurofibromatosis type 1, neurofibromatosis type 2, or neurofibromatosis type 3.

10. The method according to claim 1, wherein a pharmaceutical composition comprising a polypeptide according to claim 1 is administered by introducing a therapeutically effective amount of the composition into the blood stream of the subject.

11. The method according to claim 1, wherein the pharmaceutical composition is administered locally.

12. The method according to claim 1, wherein the polypeptide consists of an EGF-like domain of a human neuregulin protein.

13. The method according to claim 1, wherein the polypeptide consists of an EGF-like domain of a human neuregulin protein and is a soluble fragment of a neuregulin protein.

14. The method according to claim 3, wherein the polypeptide is a soluble fragment of a neuregulin protein, consists of an amino acid sequence according to any one of SEQ ID NO 9-14 or an amino acid sequence with an identity of at least 90% to any one of SEQ ID NO 9-14.

15. The method according to claim 1, wherein the polypeptide consists of an EGF-like domain of a human neuregulin protein and is a soluble fragment of a neuregulin protein and wherein the tumor is a neurofibroma or schwannoma.

* * * * *

SEQUENCE LISTING

<160> NUMBER OF SEQ ID NOS: 18

<210> SEQ ID NO 1
<211> LENGTH: 1824
<212> TYPE: DNA
<213> ORGANISM: Homo sapiens

<400> SEQUENCE: 1
atggggaaag gacgcgcggg ccgagttggc accacagcct tgcctccccg attgaaagag 60
atgaaaagcc aggaatcggc tgcaggttcc aaactagtcc ttcggtgtga aaccagttct 120
gaatactcct ctctcagatt caagtggttc aagaatggga atgaattgaa tcgaaaaaac 180
aaaccacaaa atatcaagat acaaaaaaag ccagggaagt cagaacttcg cattaacaaa 240
gcatcactgg ctgattctgg agagtatatg tgcaaagtga tcagcaaatt aggaaatgac 300
agtgcctctg ccaatatcac catcgtggaa tcaaacgaga tcatcactgg tatgccagcc 360
tcaactgaag gagcatatgt gtcttcagct acatctacat ccaccactgg gacaagccat 420
cttgtaaaat gtgcggagaa ggagaaaact ttctgtgtga atggagggga gtgcttcatg 480
gtgaaagacc tttcaaaccc ctcgagatac ttgtgcaagt gcccaaatga gtttactggt 540
gatcgctgcc aaaactacgt aatggccagc ttctacaagc atcttgggat tgaatttatg 600
gaggcggagg agctgtacca gaagagagtg ctgaccataa ccggcatctg catcgccctc 660
cttgtggtcg gcatcatgtg tgtggtggcc tactgcaaaa ccaagaaaca gcggaaaaag 720
ctgcatgacc gtcttcggca gagccttcgg tctgaacgaa acaatatgat gaacattgcc 780
aatgggcctc accatcctaa cccacccccc gagaatgtcc agctggtgaa tcaatacgta 840
tctaaaaacg tcatctccag tgagcatatt gttgagagag aagcagagac atccttttcc 900
accagtcact atacttccac agcccatcac tccactactg tcacccagac tcctagccac 960
agctggagca acggacacac tgaaagcatc ctttccgaaa gccactctgt aatcgtgatg 1020
tcatccgtag aaaacagtag gcacagcagc ccaactgggg gcccaagagg acgtcttaat 1080
ggcacaggag gccctcgtga atgtaacagc ttcctcaggc atgccagaga aacccctgat 1140
tcctaccgag actctcctca tagtgaaagg tatgtgtcag ccatgaccac cccggctcgt 1200
atgtcacctg tagatttcca cacgccaagc tcccccaaat cgccccccttc ggaaatgtct 1260 ccacccgtgt ccagcatgac ggtgtccatg ccttccatgg cggtcagccc cttcatggaa 1320
gaagagagac ctctacttct cgtgacacca ccaaggctgc gggagaagaa gtttgaccat 1380
caccctcagc agttcagctc cttccaccac aaccccgcgc atgacagtaa cagcctccct 1440
gctagcccct tgaggatagt ggaggatgag gagtatgaaa cgacccaaga gtacgagcca 1500
gcccaagagc ctgttaagaa actcgccaat agccggcggg ccaaaagaac caagcccaat 1560
ggccacattg ctaacagatt ggaagtggac agcaacacaa gctcccagag cagtaactca 1620
gagagtgaaa cagaagatga aagagtaggt gaagatacgc ctttcctggg catacagaac 1680
cccctggcag ccagtcttga ggcaacacct gccttccgcc tggctgacag caggactaac 1740
ccagcaggcc gcttctcgac acaggaagaa atccaggcca ggctgtctag tgtaattgct 1800
aaccaagacc ctattgctgt ataa 1824

<210> SEQ ID NO 2
<211> LENGTH: 1875
<212> TYPE: DNA
<213> ORGANISM: Homo sapiens

<400> SEQUENCE: 2

```
atggggaaag gacgcgcggg ccgagttggc accacagcct tgcctccccg attgaaagag      60

atgaaaagcc aggaatcggc tgcaggttcc aaactagtcc ttcggtgtga aaccagttct     120

gaatactcct ctctcagatt caagtggttc aagaatggga atgaattgaa tcgaaaaaac     180

aaaccacaaa atatcaagat acaaaaaaag ccagggaagt cagaacttcg cattaacaaa     240

gcatcactgg ctgattctgg agagtatatg tgcaaagtga tcagcaaatt aggaaatgac     300

agtgcctctg ccaatatcac catcgtggaa tcaaacgaga tcatcactgg tatgccagcc     360

tcaactgaag gagcatatgt gtcttcagag tctcccatta gaatatcagt atccacagaa     420

ggagcaaata cttcttcatc tacatctaca tccaccactg ggacaagcca tcttgtaaaa     480

tgtgcggaga aggagaaaac tttctgtgtg aatggagggg agtgcttcat ggtgaaagac     540

ctttcaaacc cctcgagata cttgtgcaag tgcccaaatg agtttactgg tgatcgctgc     600

caaaactacg taatggccag cttctacaag catcttggga ttgaatttat ggaggcggag     660

gagctgtacc agaagagagt gctgaccata accggcatct gcatcgccct ccttgtggtc     720

ggcatcatgt gtgtggtggc ctactgcaaa accaagaaac agcggaaaaa gctgcatgac     780

cgtcttcggc agagccttcg gtctgaacga aacaatatga tgaacattgc caatgggcct     840

caccatccta acccaccccc cgagaatgtc cagctggtga atcaatacgt atctaaaaac     900

gtcatctcca gtgagcatat tgttgagaga gaagcagaga catccttttc caccagtcac     960

tatacttcca cagcccatca ctccactact gtcacccaga ctcctagcca cagctggagc    1020

aacggacaca ctgaaagcat cctttccgaa agccactctg taatcgtgat gtcatccgta    1080

gaaaacagta ggcacagcag cccaactggg ggcccaagag gacgtcttaa tggcacagga    1140

ggccctcgtg aatgtaacag cttcctcagg catgccagag aaacccctga ttcctaccga    1200

gactctcctc atagtgaaag gtatgtgtca gccatgacca ccccggctcg tatgtcacct    1260

gtagatttcc acacgccaag ctcccccaaa tcgcccccttt cggaaatgtc tccacccgtg    1320

tccagcatga cggtgtccat gccttccatg gcggtcagcc ccttcatgga agaagagaga    1380

cctctacttc tcgtgacacc accaaggctg cgggagaaga agtttgacca tcaccctcag    1440

cagttcagct ccttccacca caaccccgcg catgacagta acagcctccc tgctagcccc    1500

ttgaggatag tggaggatga ggagtatgaa acgacccaag agtacgagcc agcccaagag    1560

cctgttaaga aactcgccaa tagccggcgg gccaaaagaa ccaagcccaa tggccacatt    1620

gctaacagat tggaagtgga cagcaacaca agctcccaga gcagtaactc agagagtgaa    1680

acagaagatg aaagagtagg tgaagatacg cctttcctgg gcatacagaa ccccctggca    1740

gccagtcttg aggcaacacc tgccttccgc ctggctgaca gcaggactaa cccagcaggc    1800

cgcttctcga cacaggaaga aatccaggcc aggctgtcta gtgtaattgc taaccaagac    1860

cctattgctg tataa                                                     1875
```

```
<210> SEQ ID NO 3
<211> LENGTH: 1923
<212> TYPE: DNA
<213> ORGANISM: Homo sapiens

<400> SEQUENCE: 3

atgtccgagc gcaaagaagg cagaggcaaa gggaagggca agaagaagga gcgaggctcc      60

ggcaagaagc cggagtccgc ggcgggcagc cagagcccag ccttgcctcc ccgattgaaa     120

gagatgaaaa gccaggaatc ggctgcaggt tccaaactag tccttcggtg tgaaaccagt     180
```

```
tctgaatact cctctctcag attcaagtgg ttcaagaatg ggaatgaatt gaatcgaaaa    240

aacaaaccac aaaatatcaa gatacaaaaa aagccaggga agtcagaact tcgcattaac    300

aaagcatcac tggctgattc tggagagtat atgtgcaaag tgatcagcaa attaggaaat    360

gacagtgcct ctgccaatat caccatcgtg gaatcaaacg agatcatcac tggtatgcca    420

gcctcaactg aaggagcata tgtgtcttca gagtctccca ttagaatatc agtatccaca    480

gaaggagcaa atacttcttc atctacatct acatccacca ctgggacaag ccatcttgta    540

aaatgtgcgg agaaggagaa aactttctgt gtgaatggag gggagtgctt catggtgaaa    600

gacctttcaa acccctcgag atacttgtgc aagtgccaac ctggattcac tggagcaaga    660

tgtactgaga atgtgcccat gaaagtccaa aaccaagaaa aggcggagga gctgtaccag    720

aagagagtgc tgaccataac cggcatctgc atcgccctcc ttgtggtcgg catcatgtgt    780

gtggtggcct actgcaaaac caagaaacag cggaaaaagc tgcatgaccg tcttcggcag    840

agccttcggt ctgaacgaaa caatatgatg aacattgcca atgggcctca ccatcctaac    900

ccaccccccg agaatgtcca gctggtgaat caatacgtat ctaaaaacgt catctccagt    960

gagcatattg ttgagagaga agcagagaca tccttttcca ccagtcacta tacttccaca   1020

gcccatcact ccactactgt cacccagact cctagccaca gctggagcaa cggacacact   1080

gaaagcatcc tttccgaaag ccactctgta atcgtgatgt catccgtaga aaacagtagg   1140

cacagcagcc caactggggg cccaagagga cgtcttaatg gcacaggagg ccctcgtgaa   1200

tgtaacagct tcctcaggca tgccagagaa acccctgatt cctaccgaga ctctcctcat   1260

agtgaaaggt atgtgtcagc catgaccacc ccggctcgta tgtcacctgt agatttccac   1320

acgccaagct cccccaaatc gccccccttcg gaaatgtctc cacccgtgtc cagcatgacg   1380

gtgtccatgc cttccatggc ggtcagcccc ttcatggaag aagagagacc tctacttctc   1440

gtgacaccac caaggctgcg ggagaagaag tttgaccatc accctcagca gttcagctcc   1500

ttccaccaca accccgcgca tgacagtaac agcctccctg ctagcccctt gaggatagtg   1560

gaggatgagg agtatgaaac gacccaagag tacgagccag cccaagagcc tgttaagaaa   1620

ctcgccaata gccggcgggc caaaagaacc aagcccaatg gccacattgc taacagattg   1680

gaagtggaca gcaacacaag ctcccagagc agtaactcag agagtgaaac agaagatgaa   1740

agagtaggtg aagatacgcc tttcctgggc atacagaacc ccctggcagc cagtcttgag   1800

gcaacacctg ccttccgcct ggctgacagc aggactaacc cagcaggccg cttctcgaca   1860

caggaagaaa tccaggccag gctgtctagt gtaattgcta accaagaccc tattgctgta   1920

taa                                                                 1923
```

<210> SEQ ID NO 4
<211> LENGTH: 636
<212> TYPE: DNA
<213> ORGANISM: Homo sapiens

<400> SEQUENCE: 4

```
atgtccgagc gcaaagaagg cagaggcaaa gggaagggca agaagaagga gcgaggctcc     60

ggcaagaagc cggagtccgc ggcgggcagc cagagcccag ccttgcctcc ccgattgaaa    120

gagatgaaaa gccaggaatc ggctgcaggt tccaaactag tccttcggtg tgaaaccagt    180

tctgaatact cctctctcag attcaagtgg ttcaagaatg ggaatgaatt gaatcgaaaa    240

aacaaaccac aaaatatcaa gatacaaaaa aagccaggga agtcagaact tcgcattaac    300

aaagcatcac tggctgattc tggagagtat atgtgcaaag tgatcagcaa attaggaaat    360
```

```
gacagtgcct ctgccaatat caccatcgtg gaatcaaacg agatcatcac tggtatgcca    420

gcctcaactg aaggagcata tgtgtcttca gagtctccca ttagaatatc agtatccaca    480

gaaggagcaa atacttcttc atctacatct acatccacca ctgggacaag ccatcttgta    540

aaatgtgcgg agaaggagaa aactttctgt gtgaatggag gggagtgctt catggtgaaa    600

gacctttcaa acccctcgag atacttgtgc aagtaa                              636


<210> SEQ ID NO 5
<211> LENGTH: 607
<212> TYPE: PRT
<213> ORGANISM: Homo sapiens

<400> SEQUENCE: 5

Met Gly Lys Gly Arg Ala Gly Arg Val Gly Thr Thr Ala Leu Pro Pro
1               5                   10                  15

Arg Leu Lys Glu Met Lys Ser Gln Glu Ser Ala Ala Gly Ser Lys Leu
            20                  25                  30

Val Leu Arg Cys Glu Thr Ser Ser Glu Tyr Ser Ser Leu Arg Phe Lys
        35                  40                  45

Trp Phe Lys Asn Gly Asn Glu Leu Asn Arg Lys Asn Lys Pro Gln Asn
    50                  55                  60

Ile Lys Ile Gln Lys Lys Pro Gly Lys Ser Glu Leu Arg Ile Asn Lys
65                  70                  75                  80

Ala Ser Leu Ala Asp Ser Gly Glu Tyr Met Cys Lys Val Ile Ser Lys
                85                  90                  95

Leu Gly Asn Asp Ser Ala Ser Ala Asn Ile Thr Ile Val Glu Ser Asn
            100                 105                 110

Glu Ile Ile Thr Gly Met Pro Ala Ser Thr Glu Gly Ala Tyr Val Ser
        115                 120                 125

Ser Ala Thr Ser Thr Ser Thr Thr Gly Thr Ser His Leu Val Lys Cys
    130                 135                 140

Ala Glu Lys Glu Lys Thr Phe Cys Val Asn Gly Gly Glu Cys Phe Met
145                 150                 155                 160

Val Lys Asp Leu Ser Asn Pro Ser Arg Tyr Leu Cys Lys Cys Pro Asn
                165                 170                 175

Glu Phe Thr Gly Asp Arg Cys Gln Asn Tyr Val Met Ala Ser Phe Tyr
            180                 185                 190

Lys His Leu Gly Ile Glu Phe Met Glu Ala Glu Glu Leu Tyr Gln Lys
        195                 200                 205

Arg Val Leu Thr Ile Thr Gly Ile Cys Ile Ala Leu Leu Val Val Gly
    210                 215                 220

Ile Met Cys Val Val Ala Tyr Cys Lys Thr Lys Lys Gln Arg Lys Lys
225                 230                 235                 240

Leu His Asp Arg Leu Arg Gln Ser Leu Arg Ser Glu Arg Asn Asn Met
                245                 250                 255

Met Asn Ile Ala Asn Gly Pro His His Pro Asn Pro Pro Pro Glu Asn
            260                 265                 270

Val Gln Leu Val Asn Gln Tyr Val Ser Lys Asn Val Ile Ser Ser Glu
        275                 280                 285

His Ile Val Glu Arg Glu Ala Glu Thr Ser Phe Ser Thr Ser His Tyr
    290                 295                 300

Thr Ser Thr Ala His His Ser Thr Thr Val Thr Gln Thr Pro Ser His
305                 310                 315                 320
```

```
Ser Trp Ser Asn Gly His Thr Glu Ser Ile Leu Ser Glu Ser His Ser
                325                 330                 335

Val Ile Val Met Ser Ser Val Glu Asn Ser Arg His Ser Ser Pro Thr
            340                 345                 350

Gly Gly Pro Arg Gly Arg Leu Asn Gly Thr Gly Gly Pro Arg Glu Cys
        355                 360                 365

Asn Ser Phe Leu Arg His Ala Arg Glu Thr Pro Asp Ser Tyr Arg Asp
    370                 375                 380

Ser Pro His Ser Glu Arg Tyr Val Ser Ala Met Thr Thr Pro Ala Arg
385                 390                 395                 400

Met Ser Pro Val Asp Phe His Thr Pro Ser Ser Pro Lys Ser Pro Pro
                405                 410                 415

Ser Glu Met Ser Pro Pro Val Ser Ser Met Thr Val Ser Met Pro Ser
            420                 425                 430

Met Ala Val Ser Pro Phe Met Glu Glu Glu Arg Pro Leu Leu Leu Val
        435                 440                 445

Thr Pro Pro Arg Leu Arg Glu Lys Lys Phe Asp His His Pro Gln Gln
    450                 455                 460

Phe Ser Ser Phe His His Asn Pro Ala His Asp Ser Asn Ser Leu Pro
465                 470                 475                 480

Ala Ser Pro Leu Arg Ile Val Glu Asp Glu Glu Tyr Glu Thr Thr Gln
                485                 490                 495

Glu Tyr Glu Pro Ala Gln Glu Pro Val Lys Lys Leu Ala Asn Ser Arg
            500                 505                 510

Arg Ala Lys Arg Thr Lys Pro Asn Gly His Ile Ala Asn Arg Leu Glu
        515                 520                 525

Val Asp Ser Asn Thr Ser Ser Gln Ser Ser Asn Ser Glu Ser Glu Thr
    530                 535                 540

Glu Asp Glu Arg Val Gly Glu Asp Thr Pro Phe Leu Gly Ile Gln Asn
545                 550                 555                 560

Pro Leu Ala Ala Ser Leu Glu Ala Thr Pro Ala Phe Arg Leu Ala Asp
                565                 570                 575

Ser Arg Thr Asn Pro Ala Gly Arg Phe Ser Thr Gln Glu Glu Ile Gln
            580                 585                 590

Ala Arg Leu Ser Ser Val Ile Ala Asn Gln Asp Pro Ile Ala Val
        595                 600                 605


<210> SEQ ID NO 6
<211> LENGTH: 624
<212> TYPE: PRT
<213> ORGANISM: Homo sapiens

<400> SEQUENCE: 6

Met Gly Lys Gly Arg Ala Gly Arg Val Gly Thr Thr Ala Leu Pro Pro
1               5                   10                  15

Arg Leu Lys Glu Met Lys Ser Gln Glu Ser Ala Ala Gly Ser Lys Leu
            20                  25                  30

Val Leu Arg Cys Glu Thr Ser Ser Glu Tyr Ser Ser Leu Arg Phe Lys
        35                  40                  45

Trp Phe Lys Asn Gly Asn Glu Leu Asn Arg Lys Asn Lys Pro Gln Asn
    50                  55                  60

Ile Lys Ile Gln Lys Lys Pro Gly Lys Ser Glu Leu Arg Ile Asn Lys
65                  70                  75                  80

Ala Ser Leu Ala Asp Ser Gly Glu Tyr Met Cys Lys Val Ile Ser Lys
                85                  90                  95
```

```
Leu Gly Asn Asp Ser Ala Ser Ala Asn Ile Thr Ile Val Glu Ser Asn
            100                 105                 110

Glu Ile Ile Thr Gly Met Pro Ala Ser Thr Glu Gly Ala Tyr Val Ser
        115                 120                 125

Ser Glu Ser Pro Ile Arg Ile Ser Val Ser Thr Glu Gly Ala Asn Thr
    130                 135                 140

Ser Ser Ser Thr Ser Thr Ser Thr Thr Gly Thr Ser His Leu Val Lys
145                 150                 155                 160

Cys Ala Glu Lys Glu Lys Thr Phe Cys Val Asn Gly Gly Glu Cys Phe
                165                 170                 175

Met Val Lys Asp Leu Ser Asn Pro Ser Arg Tyr Leu Cys Lys Cys Pro
            180                 185                 190

Asn Glu Phe Thr Gly Asp Arg Cys Gln Asn Tyr Val Met Ala Ser Phe
        195                 200                 205

Tyr Lys His Leu Gly Ile Glu Phe Met Glu Ala Glu Glu Leu Tyr Gln
    210                 215                 220

Lys Arg Val Leu Thr Ile Thr Gly Ile Cys Ile Ala Leu Leu Val Val
225                 230                 235                 240

Gly Ile Met Cys Val Val Ala Tyr Cys Lys Thr Lys Lys Gln Arg Lys
                245                 250                 255

Lys Leu His Asp Arg Leu Arg Gln Ser Leu Arg Ser Glu Arg Asn Asn
            260                 265                 270

Met Met Asn Ile Ala Asn Gly Pro His His Pro Asn Pro Pro Pro Glu
        275                 280                 285

Asn Val Gln Leu Val Asn Gln Tyr Val Ser Lys Asn Val Ile Ser Ser
    290                 295                 300

Glu His Ile Val Glu Arg Glu Ala Glu Thr Ser Phe Ser Thr Ser His
305                 310                 315                 320

Tyr Thr Ser Thr Ala His His Ser Thr Thr Val Thr Gln Thr Pro Ser
                325                 330                 335

His Ser Trp Ser Asn Gly His Thr Glu Ser Ile Leu Ser Glu Ser His
            340                 345                 350

Ser Val Ile Val Met Ser Ser Val Glu Asn Ser Arg His Ser Ser Pro
        355                 360                 365

Thr Gly Gly Pro Arg Gly Arg Leu Asn Gly Thr Gly Gly Pro Arg Glu
    370                 375                 380

Cys Asn Ser Phe Leu Arg His Ala Arg Glu Thr Pro Asp Ser Tyr Arg
385                 390                 395                 400

Asp Ser Pro His Ser Glu Arg Tyr Val Ser Ala Met Thr Thr Pro Ala
                405                 410                 415

Arg Met Ser Pro Val Asp Phe His Thr Pro Ser Ser Pro Lys Ser Pro
            420                 425                 430

Pro Ser Glu Met Ser Pro Pro Val Ser Ser Met Thr Val Ser Met Pro
        435                 440                 445

Ser Met Ala Val Ser Pro Phe Met Glu Glu Glu Arg Pro Leu Leu Leu
    450                 455                 460

Val Thr Pro Pro Arg Leu Arg Glu Lys Lys Phe Asp His His Pro Gln
465                 470                 475                 480

Gln Phe Ser Ser Phe His His Asn Pro Ala His Asp Ser Asn Ser Leu
                485                 490                 495

Pro Ala Ser Pro Leu Arg Ile Val Glu Asp Glu Glu Tyr Glu Thr Thr
            500                 505                 510
```

```
Gln Glu Tyr Glu Pro Ala Gln Glu Pro Val Lys Lys Leu Ala Asn Ser
        515                 520                 525

Arg Arg Ala Lys Arg Thr Lys Pro Asn Gly His Ile Ala Asn Arg Leu
    530                 535                 540

Glu Val Asp Ser Asn Thr Ser Ser Gln Ser Ser Asn Ser Glu Ser Glu
545                 550                 555                 560

Thr Glu Asp Glu Arg Val Gly Glu Asp Thr Pro Phe Leu Gly Ile Gln
                565                 570                 575

Asn Pro Leu Ala Ala Ser Leu Glu Ala Thr Pro Ala Phe Arg Leu Ala
            580                 585                 590

Asp Ser Arg Thr Asn Pro Ala Gly Arg Phe Ser Thr Gln Glu Glu Ile
        595                 600                 605

Gln Ala Arg Leu Ser Ser Val Ile Ala Asn Gln Asp Pro Ile Ala Val
    610                 615                 620


<210> SEQ ID NO 7
<211> LENGTH: 640
<212> TYPE: PRT
<213> ORGANISM: Homo sapiens

<400> SEQUENCE: 7

Met Ser Glu Arg Lys Glu Gly Arg Gly Lys Gly Lys Gly Lys Lys Lys
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys Cys Gln Pro Gly Phe Thr Gly Ala Arg Cys Thr Glu Asn
    210                 215                 220

Val Pro Met Lys Val Gln Asn Gln Glu Lys Ala Glu Glu Leu Tyr Gln
225                 230                 235                 240

Lys Arg Val Leu Thr Ile Thr Gly Ile Cys Ile Ala Leu Leu Val Val
                245                 250                 255

Gly Ile Met Cys Val Val Ala Tyr Cys Lys Thr Lys Lys Gln Arg Lys
            260                 265                 270
```

```
Lys Leu His Asp Arg Leu Arg Gln Ser Leu Arg Ser Glu Arg Asn Asn
        275                 280                 285

Met Met Asn Ile Ala Asn Gly Pro His His Pro Asn Pro Pro Pro Glu
    290                 295                 300

Asn Val Gln Leu Val Asn Gln Tyr Val Ser Lys Asn Val Ile Ser Ser
305                 310                 315                 320

Glu His Ile Val Glu Arg Glu Ala Glu Thr Ser Phe Ser Thr Ser His
                325                 330                 335

Tyr Thr Ser Thr Ala His His Ser Thr Thr Val Thr Gln Thr Pro Ser
            340                 345                 350

His Ser Trp Ser Asn Gly His Thr Glu Ser Ile Leu Ser Glu Ser His
        355                 360                 365

Ser Val Ile Val Met Ser Ser Val Glu Asn Ser Arg His Ser Ser Pro
    370                 375                 380

Thr Gly Gly Pro Arg Gly Arg Leu Asn Gly Thr Gly Gly Pro Arg Glu
385                 390                 395                 400

Cys Asn Ser Phe Leu Arg His Ala Arg Glu Thr Pro Asp Ser Tyr Arg
                405                 410                 415

Asp Ser Pro His Ser Glu Arg Tyr Val Ser Ala Met Thr Thr Pro Ala
            420                 425                 430

Arg Met Ser Pro Val Asp Phe His Thr Pro Ser Ser Pro Lys Ser Pro
        435                 440                 445

Pro Ser Glu Met Ser Pro Pro Val Ser Ser Met Thr Val Ser Met Pro
    450                 455                 460

Ser Met Ala Val Ser Pro Phe Met Glu Glu Glu Arg Pro Leu Leu Leu
465                 470                 475                 480

Val Thr Pro Pro Arg Leu Arg Glu Lys Lys Phe Asp His His Pro Gln
                485                 490                 495

Gln Phe Ser Ser Phe His His Asn Pro Ala His Asp Ser Asn Ser Leu
            500                 505                 510

Pro Ala Ser Pro Leu Arg Ile Val Glu Asp Glu Glu Tyr Glu Thr Thr
        515                 520                 525

Gln Glu Tyr Glu Pro Ala Gln Glu Pro Val Lys Lys Leu Ala Asn Ser
    530                 535                 540

Arg Arg Ala Lys Arg Thr Lys Pro Asn Gly His Ile Ala Asn Arg Leu
545                 550                 555                 560

Glu Val Asp Ser Asn Thr Ser Ser Gln Ser Ser Asn Ser Glu Ser Glu
                565                 570                 575

Thr Glu Asp Glu Arg Val Gly Glu Asp Thr Pro Phe Leu Gly Ile Gln
            580                 585                 590

Asn Pro Leu Ala Ala Ser Leu Glu Ala Thr Pro Ala Phe Arg Leu Ala
        595                 600                 605

Asp Ser Arg Thr Asn Pro Ala Gly Arg Phe Ser Thr Gln Glu Glu Ile
    610                 615                 620

Gln Ala Arg Leu Ser Ser Val Ile Ala Asn Gln Asp Pro Ile Ala Val
625                 630                 635                 640
```

<210> SEQ ID NO 8
<211> LENGTH: 211
<212> TYPE: PRT
<213> ORGANISM: Homo sapiens

<400> SEQUENCE: 8

```
Met Ser Glu Arg Lys Glu Gly Arg Gly Lys Gly Lys Gly Lys Lys Lys
```

```
1               5                   10                  15

Glu Arg Gly Ser Gly Lys Lys Pro Glu Ser Ala Ala Gly Ser Gln Ser
            20                  25                  30

Pro Ala Leu Pro Pro Arg Leu Lys Glu Met Lys Ser Gln Glu Ser Ala
        35                  40                  45

Ala Gly Ser Lys Leu Val Leu Arg Cys Glu Thr Ser Ser Glu Tyr Ser
    50                  55                  60

Ser Leu Arg Phe Lys Trp Phe Lys Asn Gly Asn Glu Leu Asn Arg Lys
65                  70                  75                  80

Asn Lys Pro Gln Asn Ile Lys Ile Gln Lys Lys Pro Gly Lys Ser Glu
                85                  90                  95

Leu Arg Ile Asn Lys Ala Ser Leu Ala Asp Ser Gly Glu Tyr Met Cys
            100                 105                 110

Lys Val Ile Ser Lys Leu Gly Asn Asp Ser Ala Ser Ala Asn Ile Thr
        115                 120                 125

Ile Val Glu Ser Asn Glu Ile Ile Thr Gly Met Pro Ala Ser Thr Glu
    130                 135                 140

Gly Ala Tyr Val Ser Ser Glu Ser Pro Ile Arg Ile Ser Val Ser Thr
145                 150                 155                 160

Glu Gly Ala Asn Thr Ser Ser Ser Thr Ser Thr Ser Thr Thr Gly Thr
                165                 170                 175

Ser His Leu Val Lys Cys Ala Glu Lys Glu Lys Thr Phe Cys Val Asn
            180                 185                 190

Gly Gly Glu Cys Phe Met Val Lys Asp Leu Ser Asn Pro Ser Arg Tyr
        195                 200                 205

Leu Cys Lys
    210


<210> SEQ ID NO 9
<211> LENGTH: 61
<212> TYPE: PRT
<213> ORGANISM: Homo sapiens

<400> SEQUENCE: 9

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Lys His Leu Gly Ile Glu Phe
    50                  55                  60


<210> SEQ ID NO 10
<211> LENGTH: 46
<212> TYPE: PRT
<213> ORGANISM: Homo sapiens

<400> SEQUENCE: 10

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr
        35                  40                  45
```

```
<210> SEQ ID NO 11
<211> LENGTH: 35
<212> TYPE: PRT
<213> ORGANISM: Homo sapiens

<400> SEQUENCE: 11

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys
        35


<210> SEQ ID NO 12
<211> LENGTH: 33
<212> TYPE: PRT
<213> ORGANISM: Homo sapiens

<400> SEQUENCE: 12

Cys Val Asn Gly Gly Glu Cys Phe Met Val Lys Asp Leu Ser Asn Pro
1               5                   10                  15

Ser Arg Tyr Leu Cys Lys Cys Pro Asn Glu Phe Thr Gly Asp Arg Cys
            20                  25                  30

Gln


<210> SEQ ID NO 13
<211> LENGTH: 33
<212> TYPE: PRT
<213> ORGANISM: Homo sapiens

<400> SEQUENCE: 13

Cys Val Asn Gly Gly Glu Cys Phe Met Val Lys Asp Leu Ser Asn Pro
1               5                   10                  15

Ser Arg Tyr Leu Cys Lys Cys Gln Pro Gly Phe Thr Gly Ala Arg Cys
            20                  25                  30

Thr


<210> SEQ ID NO 14
<211> LENGTH: 22
<212> TYPE: PRT
<213> ORGANISM: Homo sapiens

<400> SEQUENCE: 14

Cys Val Asn Gly Gly Glu Cys Phe Met Val Lys Asp Leu Ser Asn Pro
1               5                   10                  15

Ser Arg Tyr Leu Cys Lys
            20


<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15

ccaccacctc tccattgcac                                                   20


<210> SEQ ID NO 16
<211> LENGTH: 18
<212> TYPE: DNA
<213> ORGANISM: Artificial Sequence
```

```
<220> FEATURE:
<223> OTHER INFORMATION: primer

<400> SEQUENCE: 16

atgtttagct ggcccaaa                                              18


<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17

gggccaccgc ggatataaaa                                            20


<210> SEQ ID NO 18
<211> LENGTH: 17
<212> TYPE: DNA
<213> ORGANISM: Artificial Sequence
<220> FEATURE:
<223> OTHER INFORMATION: primer

<400> SEQUENCE: 18

gaacctcatc actcgtt                                               17
```